US012622570B2

(12) United States Patent
Nielsen

(10) Patent No.: US 12,622,570 B2
(45) Date of Patent: May 12, 2026

(54) MEDICAL VISUALISATION SYSTEM AND ASSOCIATED METHODS AND SYSTEMS

(71) Applicant: AMBU A/S, Ballerup (DK)

(72) Inventor: Brian Nielsen, Næstved (DK)

(73) Assignee: AMBU A/S, Ballerup (DK)

( * ) Notice: Subject to any disclaimer, the term of this patent is extended or adjusted under 35 U.S.C. 154(b) by 182 days.

(21) Appl. No.: 18/276,861

(22) PCT Filed: Mar. 1, 2022

(86) PCT No.: PCT/EP2022/055135
§ 371 (c)(1),
(2) Date: Aug. 10, 2023

(87) PCT Pub. No.: WO2022/184704
PCT Pub. Date: Sep. 9, 2022

(65) Prior Publication Data
US 2024/0115111 A1     Apr. 11, 2024

(30) Foreign Application Priority Data

Mar. 5, 2021     (DK) ........................... PA 2021 70100

(51) Int. Cl.
*A61B 1/00*          (2006.01)
(52) U.S. Cl.
CPC ........ *A61B 1/0002* (2013.01); *A61B 1/00016* (2013.01); *A61B 1/00039* (2013.01); *A61B 1/00045* (2013.01)
(58) Field of Classification Search
CPC .............. A61B 1/0002; A61B 1/00016; A61B 1/00039; A61B 1/0045; A61B 1/00018; A61B 1/00066; A61B 1/0052
See application file for complete search history.

(56) References Cited

U.S. PATENT DOCUMENTS 4,646,721 A     3/1987  Arakawa
5,450,293 A     9/1995  Hoffman
(Continued)

FOREIGN PATENT DOCUMENTS

CN     103188987 A     7/2013
EP        1827258 B1    10/2011
(Continued)

OTHER PUBLICATIONS

Corrected International Search Report received for PCT/EP2022/055134, mailed Jul. 26, 2022, 5 pages., Jul. 26, 2022.
(Continued)

*Primary Examiner* — Timothy J Neal
(74) *Attorney, Agent, or Firm* — Faegre Drinker Biddle & Reath LLP

(57) ABSTRACT

A system and method for handling auxiliary components, including a first auxiliary component and a second auxiliary component, of a medical system, wherein each auxiliary component is configured to be coupled to a respective main device part and includes a rechargeable battery configured to power electronic components of the auxiliary component and of the respective main device part, each auxiliary component further including an auxiliary memory and an auxiliary communication interface. The method includes receiving a first auxiliary component; receiving a second auxiliary component after receiving the first auxiliary component; transmitting data from the auxiliary memory of the second auxiliary component to the auxiliary memory of the first auxiliary component; charging the rechargeable battery of the second auxiliary component; and providing the first auxiliary component for retrieval after transmitting the data from the auxiliary memory of the second auxiliary component to the auxiliary memory of the first auxiliary component.

24 Claims, 13 Drawing Sheets

(56)　　　　　　References Cited

U.S. PATENT DOCUMENTS

| | | | |
|---|---|---|---|
| 5,940,126 | A | 8/1999 | Kimura |
| 6,106,457 | A | 8/2000 | Perkins et al. |
| 6,796,939 | B1 | 9/2004 | Hirata et al. |
| 7,520,853 | B2 | 4/2009 | Amling et al. |
| 7,753,842 | B2 | 7/2010 | Glukhovsky et al. |
| 8,194,121 | B2 | 6/2012 | Blumzvig et al. |
| 8,194,122 | B2 | 6/2012 | Amling et al. |
| 8,465,421 | B2 | 6/2013 | Finkman et al. |
| 8,599,250 | B2 | 12/2013 | Amling et al. |
| 8,723,936 | B2 | 5/2014 | Amling et al. |
| 9,007,450 | B2 | 4/2015 | Amling et al. |
| 9,030,544 | B2 | 5/2015 | Tashiro et al. |
| 9,033,870 | B2 | 5/2015 | Farr et al. |
| 9,179,831 | B2 | 11/2015 | Mcgrail et al. |
| 9,386,914 | B2 | 7/2016 | Birnkrant et al. |
| 9,861,334 | B2 | 1/2018 | Tajima et al. |
| 11,265,450 | B2 | 3/2022 | Katsuki |
| 12,525,145 | B2 | 1/2026 | Jøgensen et al. |
| 2003/0195390 | A1 | 10/2003 | Graumann |
| 2003/0228553 | A1 | 12/2003 | Mandelkern et al. |
| 2004/0243448 | A1 | 12/2004 | Shoji et al. |
| 2006/0116667 | A1* | 6/2006 | Hamel .................... A61B 50/13 |
| | | | 606/1 |
| 2007/0162095 | A1 | 7/2007 | Kimmel et al. |
| 2007/0195539 | A1 | 8/2007 | Dashiell |
| 2008/0139881 | A1 | 6/2008 | Cover et al. |
| 2008/0214896 | A1 | 9/2008 | Krupa et al. |
| 2009/0076331 | A1 | 3/2009 | Konwitz et al. |
| 2009/0247824 | A1 | 10/2009 | Kawasaki et al. |
| 2009/0270679 | A1 | 10/2009 | Hoeg et al. |
| 2009/0318758 | A1 | 12/2009 | Farr et al. |
| 2010/0014174 | A1 | 1/2010 | Togino |
| 2010/0097453 | A1 | 4/2010 | Endo et al. |
| 2010/0141744 | A1* | 6/2010 | Amling .............. A61B 1/00055 |
| | | | 348/E7.085 |
| 2010/0208054 | A1 | 8/2010 | Farr |
| 2011/0222746 | A1 | 9/2011 | Kotula et al. |
| 2011/0243116 | A1 | 10/2011 | Endo et al. |
| 2012/0134410 | A1 | 5/2012 | Kawasaki et al. |
| 2012/0162472 | A1 | 6/2012 | Amling et al. |
| 2012/0209071 | A1 | 8/2012 | Bayer et al. |
| 2012/0246374 | A1 | 9/2012 | Fino |
| 2012/0289858 | A1 | 11/2012 | Ouyang et al. |
| 2013/0092173 | A1 | 4/2013 | Alexander et al. |
| 2013/0103907 | A1 | 4/2013 | Katori et al. |
| 2013/0204085 | A1 | 8/2013 | Alexander et al. |
| 2014/0003418 | A1 | 1/2014 | Khait et al. |
| 2014/0135576 | A1 | 5/2014 | Hebert |
| 2014/0275763 | A1* | 9/2014 | King .................. A61B 1/00105 |
| | | | 600/110 |
| 2015/0035967 | A1 | 2/2015 | Wodnicki et al. |
| 2015/0293877 | A1 | 10/2015 | Liang et al. |
| 2016/0000300 | A1 | 1/2016 | Williams |
| 2016/0048536 | A1 | 2/2016 | Di et al. |
| 2016/0066770 | A1 | 3/2016 | Barbato et al. |
| 2016/0073855 | A1 | 3/2016 | Farr et al. |
| 2016/0213236 | A1 | 7/2016 | Hruska et al. |
| 2016/0299629 | A1 | 10/2016 | Doyle et al. |
| 2016/0344992 | A1 | 11/2016 | D'Alfonso et al. |
| 2017/0095297 | A1 | 4/2017 | Richmond et al. |
| 2017/0209027 | A1 | 7/2017 | Raj et al. |
| 2017/0280988 | A1 | 10/2017 | Barbato et al. |
| 2017/0311777 | A1 | 11/2017 | Hirayama et al. |
| 2018/0084986 | A1 | 3/2018 | Ochi et al. |
| 2018/0220873 | A1 | 8/2018 | Tani |
| 2018/0296067 | A1 | 10/2018 | Amling et al. |
| 2018/0296289 | A1 | 10/2018 | Rodriguez-Navarro et al. |
| 2019/0052560 | A1 | 2/2019 | Smith |
| 2019/0104922 | A1 | 4/2019 | Kasumi |
| 2019/0133430 | A1 | 5/2019 | Inglis et al. |
| 2019/0142256 | A1 | 5/2019 | Zhao et al. |
| 2019/0200844 | A1 | 7/2019 | Shelton et al. |
| 2019/0238791 | A1 | 8/2019 | Ingle |
| 2019/0261844 | A1 | 8/2019 | Walker et al. |
| 2019/0313881 | A1 | 10/2019 | Francher |

| | | | |
|---|---|---|---|
| 2019/0320879 | A1 | 10/2019 | Langell et al. |
| 2019/0335987 | A1 | 11/2019 | Cook |
| 2019/0350438 | A1 | 11/2019 | Masuno et al. |
| 2020/0113412 | A1 | 4/2020 | Jensen |
| 2020/0273575 | A1 | 8/2020 | Wolf et al. |
| 2020/0287899 | A1 | 9/2020 | Koizumi et al. |
| 2020/0305684 | A1 | 10/2020 | Hagihara |
| 2020/0405124 | A1 | 12/2020 | Sonnenborg et al. |
| 2021/0105467 | A1 | 4/2021 | Tani |
| 2021/0113059 | A1 | 4/2021 | Kasumi |
| 2021/0259522 | A1 | 8/2021 | Ubbesen et al. |
| 2021/0266435 | A1 | 8/2021 | Katsuki |
| 2021/0338040 | A1 | 11/2021 | Michihata et al. |
| 2021/0358086 | A1 | 11/2021 | Jørgensen et al. |
| 2022/0039634 | A1 | 2/2022 | Williams |
| 2022/0104822 | A1 | 4/2022 | Shelton et al. |
| 2022/0230643 | A1 | 7/2022 | Pai et al. |
| 2023/0037178 | A1 | 2/2023 | Kamon |
| 2024/0108207 | A1 | 4/2024 | Yazdi et al. |

FOREIGN PATENT DOCUMENTS

| | | |
|---|---|---|
| EP | 2445210 A1 | 4/2012 |
| EP | 2286718 B1 | 12/2013 |
| EP | 2778999 A2 | 9/2014 |
| EP | 3417758 A1 | 12/2018 |
| EP | 3636133 A1 | 4/2020 |
| JP | 4918599 B2 | 4/2012 |
| JP | 2012-090974 A | 5/2012 |
| WO | 2008/063565 A2 | 5/2008 |
| WO | 2015/163942 A1 | 10/2015 |
| WO | 2019/198364 A1 | 10/2019 |
| WO | 2019/211938 A1 | 11/2019 |
| WO | 2020/031717 A1 | 2/2020 |
| WO | 2020/039716 A1 | 2/2020 |

OTHER PUBLICATIONS

Examination and Search Report for Denmark Application No. DK PA202170102, mailed on Jun. 21, 2021, 9 pages.

Examination and Search Report for Denmark Application No. PA202170098, mailed on May 18, 2021, 12 pages.

Examination and Search Report for Denmark Application No. PA202170099, mailed on Jun. 25, 2021, 8 pages.

Examination and Search Report for Denmark Application No. PA202170100, mailed on Jun. 25, 2021, 8 pages.

Examination and Search Report for Denmark Application No. PA202170101, mailed on Jun. 21, 2021, 9 pages.

International Search Report and Written Opinion received for PCT Patent Application No. PCT/EP2022/055139, mailed on Jun. 22, 2022, 14 pages.

International Search Report and Written Opinion received for PCT Patent Application No. PCT/EP2022/055133, mailed on Jun. 3, 2022, 10 pages.

International Search Report and Written Opinion received for PCT Patent Application No. PCT/EP2022/055134, mailed on Jul. 26, 2022, 14 pages.

International Search Report and Written Opinion received for PCT Patent Application No. PCT/EP2022/055135, mailed on Jun. 22, 2022, 9 pages.

International Search Report and Written Opinion received for PCT Patent Application No. PCT/EP2022/055136, mailed on Aug. 5, 2022, 17 pages.

Office Action in related U.S. Appl. No. 18/240,847 dated May 30, 2025, 28 pages.

Office Action in related U.S. Appl. No. 18/276,868 dated Aug. 4, 2025, 15 pages.

Office Action in related U.S. Appl. No. 18/277,303 dated Aug. 27, 2025, 32 pages.

Office Action in related U.S. Appl. No. 18/276,866 dated Jan. 16, 2026, 26 pages.

Office Action in related U.S. Appl. No. 18/276,868 dated Feb. 20, 2026, 22 pages.

(56)                 References Cited

OTHER PUBLICATIONS

Office Action in related U.S. Appl. No. 18/277,312 dated Dec. 17, 2025, 31 pages.

* cited by examiner

510

700

402

150

402'

150

1

MEDICAL VISUALISATION SYSTEM AND ASSOCIATED METHODS AND SYSTEMS

CROSS REFERENCE TO RELATED APPLICATIONS

This application is a National Phase entry under 35 U.S.C. § 371 of International Application No. PCT/EP2022/055135, filed Mar. 1, 2022, which claims the benefit of and priority from Danish Patent Application No. PA 2021 70100, filed Mar. 5, 2021. The foregoing applications are incorporated by reference herein in their entirety.

The present disclosure relates to a medical visualisation system and elements thereof. Particularly a medical visualisation system comprising a plurality of auxiliary components for medical visualisation devices, and a method and system for handling the auxiliary components.

BACKGROUND

Wireless medical devices that utilize wireless communication from a medical device to a processing device is known in the art.

However, these technical solutions are not widespread as commercially available products, and particularly they are not widespread when it comes to single use products. There exists a vast spectrum of technical solutions providing a wireless communication link, but few fulfil the needs for medical devices at hospital settings.

For instance, not all communication frequencies may be used at hospitals and for medical devices, and in particular visualisation devices, such as endoscopes, very low latency is an important parameter. Moreover, usability and cost are driving factors defining suitable technical solutions.

SUMMARY

The present disclosure relates to a visualisation device, such as an endoscope, and a visualisation system, such as an endoscope system. Particularly, but not exclusively the visualisation device may be a disposable camera endoscope. Alternatively, the visualisation device may be a video laryngoscope. The visualisation system may further comprise a monitor device for being connected to the visualisation device, e.g. the monitor device may be configured to receive image data from the visualisation device.

It is an object of the present disclosure to provide a solution which at least improve the solutions of the prior art. Particularly, it is an object of the present disclosure to provide a medical visualisation system and components thereof to enhance flexibility and usability of the system. For example, the present disclosure provides solutions for enabling wireless transmission of video data from a medical visualisation device, such as an endoscope or a laryngoscope, to a monitor device or other suitable equipment.

Accordingly, a medical visualisation system and elements thereof are disclosed. The medical visualisation system may comprise one or more or all of the elements disclosed in the following.

A medical visualisation device is disclosed. The medical visualisation system may comprise the medical visualisation device. The medical visualisation device may completely or partly be a single-use product. The medical visualisation device may be an endoscope. For example, the medical visualisation device may comprise a handle and an insertion tube extending from the handle to a distal tube portion. The handle may comprise a control button adapted to receive an input in a first input direction and/or in a second input direction. The touch input in the first input direction may cause a bendable section of the insertion tube to bend in a first bending direction. The touch input in the second input direction may cause the bendable section to bend in a second bending direction. Other examples of the medical visualisation device may be a laryngoscope or an endotracheal tube with integrated camera.

The medical visualisation device comprises an image sensor adapted to generate image data indicative of a view from the medical visualisation device and a light emitter adapted to provide illumination of the view. The view may be a view from the distal tube portion of the insertion tube. The light emitter may be an LED, an optical fibre, or similar element known to provide illumination. The medical visualisation device further comprises a device processing unit adapted to receive the image data from the image sensor and optionally encode the image data to provide encoded image data based on the image data. The device processing unit may comprise an image signal processor (ISP), a complex programmable logic device (CPLD), a field-programmable gate array (FPGA) and/or other suitable processing unit elements. The device processing unit may comprise memory, such as buffer memory.

The medical visualisation device comprises a device communication interface. For example, the medical visualisation device may comprise a device wireless communication module adapted to communicate with a monitor wireless communication module of a monitor device, such as the monitor device also disclosed herein. The device wireless communication module may be connected to the device processing unit. The device wireless communication module is adapted to receive the image data and/or the encoded image data from the device processing unit and transmit the image data and/or the encoded image data using a downstream data channel to the monitor wireless communication module.

Also disclosed is an auxiliary component. The medical visualisation system may comprise the auxiliary component. The auxiliary component may be couplable to a main device part to form the disclosed medical visualisation device, wherein the main device part comprises the image sensor and the light emitter and a main coupling part. The main device part may further comprise the handle and/or the insertion tube, as described above.

The auxiliary component may be couplable to the main device part. The auxiliary component comprises an auxiliary coupling part adapted to couple with the main coupling part. The auxiliary component further may comprise the device processing unit. The auxiliary component may further comprise one or more auxiliary communication interfaces. For example, the auxiliary component may comprise the device wireless communication module.

The main device part may be a single-use product. The auxiliary component may be a re-usable product. Hence, the auxiliary component may be adapted to be coupled to a plurality of main device parts.

The auxiliary component or part thereof may be a dongle for insertion into a designated receiver of the main device part. Alternatively or additionally, the auxiliary component or part thereof may be a wearable device, such as a wristwatch or an armband.

Also disclosed is a monitor device. The medical visualisation system may comprise the monitor device. The monitor device is operable to receive image data from a medical visualisation device, such as the disclosed medical visualisation device. The monitor device comprises a first housing. The medical visualisation system may comprise a display. The monitor device may comprise the display, e.g. accommodated in the first housing or couplable to the first housing, e.g. the display may be supported by the first housing or affixed to the first housing. Alternatively, the monitor device, such as the first housing, may be couplable to the display, e.g. the display may be an external display. For example, the monitor device may be devoid of a display. The display, whether forming part of the monitor device or not, may be a touch sensitive display.

The monitor device further comprises one or more monitor communication interfaces. For example, the monitor device may comprise a monitor wireless communication module adapted to communicate with a device wireless communication module of the medical visualisation device. The monitor wireless communication module may be adapted to receive image data and/or encoded image data using a downstream data channel from the device wireless communication module to the monitor wireless communication module.

The monitor device further comprises a monitor processing unit adapted to receive the image data and/or the encoded image data from the monitor wireless communication module, optionally decode the encoded image data, and cause the display to display a live representation of the image data.

The monitor processing unit may comprise a complex programmable logic device (CPLD), a field-programmable gate array (FPGA) and/or other suitable processing unit elements. The monitor processing unit may comprise memory, such as buffer memory.

The monitor device may further comprise a monitor memory. The monitor memory may be connected to the monitor processing unit. The monitor processing unit may be adapted to read and/or write data from the monitor memory. The monitor memory may be any suitable electronic memory. The monitor memory may be non-volatile memory, such as a Flash memory.

The auxiliary component may comprise auxiliary memory. The auxiliary memory may be non-transitive memory.

The present disclosure provides solutions for transferring data between auxiliary components, such as to enable replacement of one auxiliary component, e.g. storing personal and/or unique information, with another auxiliary component. For example, this may be needed if an auxiliary component is running low on battery.

A first auxiliary component, such as the disclosed auxiliary component, and a second auxiliary component, such as the disclosed auxiliary component, may be adapted to transmit, via respective auxiliary communication interfaces, data from the auxiliary memory of the second auxiliary component to the auxiliary memory of the first auxiliary component. The transmission may be in response to receiving, at an auxiliary user interface of the first auxiliary component and/or an auxiliary user interface of the second auxiliary component, one or more user inputs indicative of a request to transmit the data from the auxiliary memory of the second auxiliary component to the auxiliary memory of the first auxiliary component.

Also disclosed is a method for handling auxiliary components, such as a plurality of the disclosed auxiliary component, e.g. including a first auxiliary component, such as the disclosed auxiliary component, and a second auxiliary component, such as the disclosed auxiliary component. The method may comprise handling the auxiliary components by use of the below disclosed handling system.

The method comprises receiving a first auxiliary component, receiving a second auxiliary component, e.g. after receiving the first auxiliary component, and transmitting data from the auxiliary memory of the second auxiliary component to the auxiliary memory of the first auxiliary component. The method may further comprise providing the first auxiliary component for retrieval after transmitting the data from the auxiliary memory of the second auxiliary component to the auxiliary memory of the first auxiliary component.

Also disclosed is a handling system for handling auxiliary components, such as a plurality of the disclosed auxiliary component, e.g. including a first auxiliary component, such as the disclosed auxiliary component, and a second auxiliary component, such as the disclosed auxiliary component. The handling system may be used to perform the disclosed method for handling auxiliary components.

The handling system comprises a first system communication interface adapted to couple with an auxiliary communication interface of the first auxiliary component and a second system communication interface adapted to couple with an auxiliary communication interface of the second auxiliary component. The handling system is adapted to, via the first system communication interface and/or the second system communication interface, cause transmittal of data from the auxiliary memory of the second auxiliary component to the auxiliary memory of the first auxiliary component.

The handling system may further be adapted to, via the first system communication interface and/or the second system communication interface, cause transmittal of data from the auxiliary memory of the first auxiliary component to the auxiliary memory of the second auxiliary component.

The medical visualisation system may comprise a plurality of medical visualisation devices, e.g. comprising a first medical visualisation device and a second medical visualisation device, each of which may comprise some or all of the features as described in relation to the medical visualisation device disclosed herein. The plurality of medical visualisation devices may be different visualisation devices. In an example, the first medical visualisation device may be an endoscope comprising a flexible tube and the second medical visualisation device may be a video laryngoscope.

The plurality of medical visualisation devices may be different types, e.g. configured for different clinical purposes. For example, the first medical visualisation device may be a first device type configured for a first clinical purpose, and the second medical visualisation device may be a second device type configured for a second clinical purpose. An exemplary clinical purpose may be urology. For example, the first device type or the second device type may be a urology endoscope, such as a cystoscope or a ureteroscope. Another exemplary clinical purpose may be gastroenterology. For example, the first device type or the second device type may be a gastro-intestinal endoscope, such as a gastroscope, a duodenoscope or a colonoscope. Yet another exemplary clinical purpose may be pulmonology. For example, the first device type or the second device type may be a pulmonology endoscope, such as a bronchoscope.

The plurality of medical visualisation devices may comprise image sensors of same or different image sensor type. For example, the image sensor of the first medical visualisation device may be a first image sensor type and the image sensor of the second medical visualisation device may be a second image sensor type. Alternatively the image sensor of the second medical visualisation device may be the first image sensor type. Alternatively or additionally, the image sensor of a third medical visualisation device may be a third image sensor type or the second image sensor type. The image sensor types may differ on various aspects, e.g. by power supply voltage, by image resolution, by physical size etc.

The auxiliary component may be couplable to the plurality of medical visualisation devices, e.g. the auxiliary component may be couplable both to the first medical visualisation device and the second medical visualisation device and/or the third medical visualisation device. Hence, for example, one auxiliary component may be couplable to a range of different medical visualisation devices.

BRIEF DESCRIPTION OF THE FIGURES

Embodiments of the disclosure will be described in more detail in the following with regard to the accompanying figures. The figures show one way of implementing the present disclosure and are not to be construed as being limiting to other possible embodiments falling within the scope of the attached claim set.

DETAILED DESCRIPTION

Figure 1A:
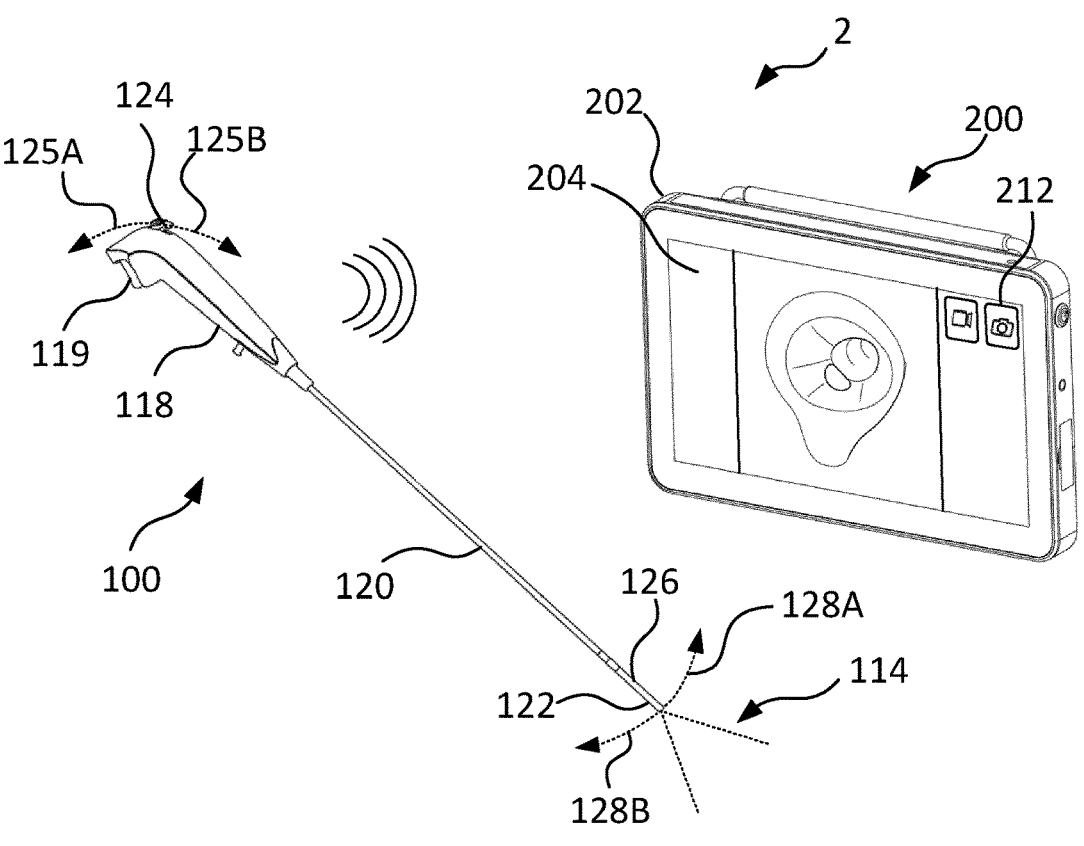
FIG. 1 schematically illustrates an exemplary medical visualisation system.

Further details of the aspects of the disclosure, as set out above, are provided in the following. Details and/or advantages may be practiced in any embodiment and/or aspect even if not so illustrated, or if not so explicitly described.

The main part of the medical visualisation device and the auxiliary component may be couplable by a main coupling part of the main part and an auxiliary coupling part of the auxiliary component. The auxiliary coupling part may be adapted to couple with the main coupling part. The main coupling part may be adapted to couple with the auxiliary coupling part. The main coupling part may have one or more main terminals electrically connected to the light emitter and image sensor. The auxiliary coupling part may comprise one or more auxiliary terminals adapted to connect to the one or more main terminals, e.g. when the auxiliary coupling part is coupled with the main coupling part. The one or more auxiliary communication interfaces may comprise the auxiliary coupling part and/or the one or more auxiliary terminals of the auxiliary coupling part. The one or more auxiliary terminals and/or the one or more main terminals may be exposed terminals, i.e. adapted to contact opposing terminals.

The device processing unit may be electrically connected to the one or more auxiliary terminals and may be adapted to receive the image data from the image sensor, e.g. via the one or more auxiliary terminals, e.g. when the auxiliary component is coupled to the main device part, such as when the auxiliary coupling part is coupled with the main coupling part.

The auxiliary component may comprise a battery, such as a rechargeable battery, e.g. a Li-Ion battery or another suitable battery. The battery may be adapted to power the device processing unit and/or the device wireless communication module. The battery may be electrically connected to the device processing unit and/or the device wireless communication module, such as to power the device processing unit and/or the device wireless communication module. The battery may be electrically connected to the one or more auxiliary terminals. The battery may be adapted to power the image sensor and light emitter of the main device part, e.g. via the one or more auxiliary terminals, e.g. when the auxiliary component is coupled to the main device part, such as when the auxiliary coupling part is coupled with the main coupling part. The battery may, when fully charged, comprise a battery capacity allowing at least 2 hours of continued usage of the medical visualisation device.

The auxiliary component may comprise a battery indicator indicative of remaining capacity of the battery. The battery indicator may be an LED or other suitable means for providing an indication of remaining battery capacity. Thus, an operator of the medical visualisation device may be alerted if battery capacity is running low. The battery indicator may comprise a plurality of bars (e.g. five) indicative of capacity of the battery, e.g. fewer bars displayed for less battery capacity. Alternatively or additionally, the battery indicator may indicate battery capacity by being lit in different colours, e.g. green (indicative of full or near full charge), yellow (medium capacity), red (low capacity). Bars and colour may be combined. For example, by the five following levels of indication, from full capacity to near empty: Five bars and green, four bars and green, three bars and yellow, two bars and yellow, one bar and red. The battery indicator may be flashing, e.g. red, when the battery capacity is below a threshold capacity.

The battery indicator may be adapted to receive a user input, e.g. a touch input, and in response to the user input, the battery indicator may provide a signal indicative of battery capacity. For example, an LED indicator may light up in a colour, e.g. green/yellow/red, indicative of estimated battery capacity.

The auxiliary component may comprise an auxiliary housing. The auxiliary housing may enclose elements of the auxiliary component, such as the device processing unit and/or the device wireless communication module and/or the battery. The auxiliary housing may be fluid-tight to the outside, e.g. such that the auxiliary component is adapted for wet cleaning, e.g. by immersion in a liquid. For example, the auxiliary housing may be surface coated with a sealing liquid, e.g. by immersion in the sealing liquid, to make the auxiliary housing fluid-tight to the outside. Alternatively or additionally, the terminals of the auxiliary component may be provided by insert moulding, whereby the conductive terminals may be provided, during moulding, in respective positions in the mould for moulding, e.g. by injection moulding, the auxiliary housing. The auxiliary housing may be IP67 compliant.

The main device part, such as the main coupling part of the main device part, may comprise a safety-circuit. The safety circuit may be adapted to prevent excessive current to elements of the main device part, such as the light emitter and/or image sensor. For example, the one or more main terminals may be electrically connected to the elements of the main device part, such as the light emitter and/or the image sensor, via the safety circuit.

The main device part, such as the main coupling part of the main device part, may comprise a device identifier comprising device identifier information, e.g. to allow identification of the main device part, e.g. including serial number, batch number, device type, etc. The device processing unit may be adapted to obtain the device identifier information from the device identifier. The device processing unit and/or the monitor processing unit may be adapted to configure the auxiliary component and/or the monitor device to be configured according to the obtained device identifier information, e.g. such as to be compatible with the main device part.

The device identifier may include an electronically readable memory, such as an EPROM, RFID, NFC or similar. In other examples the device identifier may be a QR-code, bar-code or similar. The device identifier, or the electronically readable memory of the device identifier, may be connected to the one or more main terminals. Alternatively, the device identifier may be readable without the necessity to establish an electrical contact. For example, the device identifier may be readable by means of a short-range communication circuit, such as an RFID or NFC circuit.

Providing the main device part with a safety circuit and/or a device identifier facilitates that the auxiliary component may be used with different disposable parts, e.g. gastroscopes, bronchoscopes, laryngoscopes etc.

The device wireless communication module and/or the monitor wireless communication module may be adapted to communicate wirelessly, such as to wirelessly receive and/or wirelessly transmit data, e.g. image data, encoded image data and/or other data described herein. The device wireless communication module and/or the monitor wireless communication module may be adapted to communicate using a radio frequency of more than 10 GHz, such as using a radio frequency between 57-66 GHz, such as between 57-64 GHz, such as between 57.05-64 GHz, such as between 59-64 GHz, such as between 59.4-63.56, such as between 59.4-62.9 GHz. These frequencies facilitate high bandwidth and low latency for the live images to be displayed on the display. Furthermore, the exemplary frequencies have a limited range making it advantageous to use for medical visualisation procedures, as this lowers the risk of the image data being interceptable or interfering with other procedures outside the room wherein the procedure is being performed.

The auxiliary memory may store initial data, e.g. for being loaded by the monitor device. The auxiliary component may be enablable to transmit the initial data to the monitor device using an auxiliary communication interface, such as the device wireless communication module or other suitable communication interfaces for transmitting the initial data to the monitor device. The monitor processing unit may be adapted to receive the initial data and adjust one or more parameters of the medical visualisation system based on the initial data.

The initial data may comprise patient data, e.g. of the patient on which the procedure is about to be performed, such as patient name, social security number, medical history, information about allergies, etc. The monitor processing unit may be adapted to associate the patient data with the image data and/or any captured image data files or video sequence files. Thus, the auxiliary component may be adapted to follow the patient, and upon performing a procedure, data of the patient may be automatically received by the monitor device.

Alternatively or additionally, the initial data may comprise operator data, e.g. indicative of the operator performing the medical visualisation procedure, such as name, identification number, etc. The monitor processing unit may be adapted to associate the operator data with the image data and/or any captured image data files or video sequence files. Thus, the auxiliary component may be adapted to follow the operator, and upon performing a procedure, data of the operator may be automatically received by the monitor device. The operator data may alternatively or additionally be indicative of a username or other logon credentials of the operator, and the monitor processing unit may be adapted to initiate a logon procedure of the monitor device using the username or other logon credentials indicated by the initial data. Thereby, the user may more easily logon to the monitor device and/or an associated IT-system, e.g. by only providing a password or other authentication method, which may include contactless authentication methods, such as biometric recognition, such as facial recognition or similar. Hence the logon procedure may be faster as the username or other logon credentials need not be entered manually.

Alternatively or additionally, the initial data may comprise operator setup data, e.g. associated with the operator performing the medical visualisation procedure.

The operator setup data may include image parameters, e.g. including one or more of settings of hue, saturation, brightness, contrast, and sharpness. The monitor processing unit may, in response to receiving the initial data, adjusts image parameters of the live representation of the image data displayed on the display in accordance with the image parameters of the operator setup data. Thus, the system may conveniently adjust parameters to be in accordance with preferences of the operator, thereby reducing unnecessary time to setup the monitor device in accordance with individual preferences of an operator.

The medical visualisation system, such as the monitor device and/or the medical visualisation device may, as previously described, comprise one or more buttons adapted to receive user inputs. The operator setup data may include button settings indicative of functions assigned to one or more buttons of the medical visualisation system, e.g. on the handle of the main device part or on the monitor device. The monitor processing unit may, in response to receiving the initial data, assign functions to the one or more of the buttons in accordance with the button settings of the operator setup data. Thus, the system may conveniently setup the devices in accordance with preferences of the operator, thereby reducing unnecessary manual setup time prior to a procedure.

The monitor processing unit and/or the device processing unit may be adapted to perform tasks based on spoken inputs. The operator setup data may include voice control data associated with the operator, e.g. including keywords, training data etc. The monitor processing unit, after receiving the initial data, may identify tasks to be performed based on the spoken inputs and the voice control data of the initial data.

The present disclosure provides solution for transferring data, such as the initial data, between auxiliary components, such as to enable replacement of one auxiliary component, storing personal and unique information, with another auxiliary component. For example, this may be needed if an auxiliary component is running low on battery.

As described above, the present disclosure provides method and a handling system for causing transmission of data, e.g. the initial data, from the auxiliary memory of a second auxiliary component to the auxiliary memory of a first auxiliary component. The method and handling system may further cause transmittal of data from the auxiliary memory of the first auxiliary component to the auxiliary memory of the second auxiliary component.

While or after transmission of data, the rechargeable battery of the second auxiliary component and/or the first auxiliary component may be charging. The handling system may comprise a system charging circuit adapted to charge the rechargeable battery of the first auxiliary component and/or the second auxiliary component. The handling system may comprise a first system charging circuit adapted to charge the rechargeable battery of the first auxiliary component and/or a second system charging circuit adapted to charge the rechargeable battery of the second auxiliary component.

It is an advantage of the handling system that it reduces or avoid the need to employ buttons or similar on the auxiliary components, as the user may manage the auxiliary components through the handling system.

It is a further advantage of the handling system that in addition to facilitate transfer of data between auxiliary components, it also facilitates charging of the auxiliary component from which the data is being transferred. As the most likely scenario for wanting to transfer the data is that the currently used auxiliary component is running low on power, it is advantageous that the handling system provides both transfer of data, as well as charging of the auxiliary component from which data is transferred. Thereby, the auxiliary component from which data is transferred may be ready at the handling system for the next time there is a need to swap an auxiliary component.

The handling system may comprise a system processing unit. The system processing unit may be adapted to cause the transmittal of the data. For example, the system processing unit may send, e.g. via the first system communication interface and/or the second system communication interface, appropriate commands to the first auxiliary component and/or second auxiliary component, to control the transmission of data from the auxiliary memory of the second auxiliary component to the auxiliary memory of the first auxiliary component. Alternatively or additionally, to transmit the data, the system processing unit may be adapted to, e.g. via the second system communication interface, read or receive the data of the auxiliary memory of the second auxiliary component, and, e.g. via the first system communication interface, write or transmit the data from the auxiliary memory of the second auxiliary component to the auxiliary memory of the first auxiliary component.

Each of the auxiliary components may comprises a short-range communication circuit, e.g. near field communication (NFC), Bluetooth or similar. For example, the one or more auxiliary communication interfaces may include a short-range communication circuit. The handling system may be adapted to, e.g. via the first system communication interface and/or the second system communication interface, to cause transmittal of the data from the auxiliary memory of the second auxiliary component to the auxiliary memory of the first auxiliary component by wireless communication between the short-range communication circuit of the first auxiliary component and the short-range communication circuit of the second auxiliary component.

Alternatively or additionally, the first auxiliary component and the second auxiliary component may be adapted to transmit, e.g. via the short range communication circuits, the data from the auxiliary memory of the second auxiliary component to the auxiliary memory of the first auxiliary component, in response to receiving, at auxiliary user interface(s) of the first auxiliary component and/or second auxiliary component, one or more user inputs indicative of a request to transmit the data from the auxiliary memory of the second auxiliary component to the auxiliary memory of the first auxiliary component. Thus, the transmission of the data between the auxiliary components may be provided without the need for further components, such as the handling system.

The one or more user inputs indicative of a request to transmit the data from the auxiliary memory of the second auxiliary component to the auxiliary memory of the first auxiliary component may comprise receiving a first user input at the auxiliary user interface of the first auxiliary component and while or after receiving the first user input at the auxiliary user interface of the first auxiliary component receiving a second user input at the auxiliary user interface of the second auxiliary component.

After transmitting the data to the auxiliary memory of the first auxiliary component, the data at the auxiliary memory of the first auxiliary component may be validated, such as to make sure the data was successfully transmitted and was not corrupted. The handling system, such as the system processing unit, may be adapted to validate the data of the auxiliary memory of the first auxiliary component after transmittal of the data to the auxiliary memory of the first auxiliary component.

After transmitting the data to the auxiliary memory of the first auxiliary component, and optionally after validating the data at the auxiliary memory of the first auxiliary component, the data at the auxiliary memory of the second auxiliary component may be deleted. The handling system, such as the system processing unit, may be adapted to delete the data from the auxiliary memory of the second auxiliary component, e.g. after transmittal of the data to the auxiliary memory of the first auxiliary component and optionally after validating the data at the auxiliary memory of the first auxiliary component.

The handling system may comprise a plurality of component positions, e.g. including a first component position adapted to receive the first auxiliary component and a second component position adapted to receive the second auxiliary component. The plurality of component positions may include further component positions, such as a third component position and/or a fourth component positions, such as to allow charging of a higher number of auxiliary components, thereby increasing the likelihood that a fully charged auxiliary component may be available at the handling system. In case of more than one auxiliary component being available to receive the data, the handling system may be adapted to cause transmission of the data to the auxiliary component with the mostly charged battery.

A user input, e.g. at a transmit button, may be received, indicating that a user requests transmitting the data from the auxiliary memory of the second auxiliary component to the auxiliary memory of the first auxiliary component. The data from the auxiliary memory of the second auxiliary component to the auxiliary memory of the first auxiliary component may be transmitted in response to receipt of the user input. The handling system may comprise one or more transmit buttons, e.g. including a first transmit button and/or a second transmit button. The first transmit button may indicate transmission of the data from the second auxiliary component to the first auxiliary component, e.g. by an arrow. The second transmit button may indicate transmission of the data from the first auxiliary component to the second auxiliary component, e.g. by an arrow. The handling system may be adapted to cause the transmittal of the data from the auxiliary memory of the second auxiliary component to the auxiliary memory of the first auxiliary component, in response to a user pressing the first transmit button, e.g. for a predetermined amount of time, e.g. 3 seconds. The handling system may be adapted to cause the transmittal of the data from the auxiliary memory of the first auxiliary component to the auxiliary memory of the second auxiliary component, in response to a user pressing the second transmit button, e.g. for a predetermined amount of time, e.g. 3 seconds.

The handling system may comprise one or more battery indicators, e.g. adapted to display a visual indication of estimated battery capacity of the rechargeable battery of the first auxiliary component and/or the second auxiliary component. For example, one or more battery indicators may include a first battery indicator adapted to display a visual indication of estimated battery capacity of the rechargeable battery of the first auxiliary component, and/or the handling system may comprise a second battery indicator adapted to display a visual indication of estimated battery capacity of the rechargeable battery of the second auxiliary component.

The battery indicator(s) may be an LED or other suitable means for providing an indication of remaining battery capacity. The battery indicator(s) may comprise a plurality of bars (e.g. five) indicative of capacity of the battery, e.g. fewer bars displayed for less battery capacity. Alternatively or additionally, the battery indicator(s) may indicate battery capacity by being lit in different colours, e.g. green (indicative of full or near full charge), yellow (medium capacity), red (low capacity). Bars and colour may be combined. For example, by the five following levels of indication, from full capacity to near empty: Five bars and green, four bars and green, three bars and yellow, two bars and yellow, one bar and red.

The data from the auxiliary memory of the second auxiliary component may be stored at an external memory, such as a server, e.g. a webserver. The handling system may be connectable to an external memory, such as a server, e.g. a webserver. The handling system may be adapted to, e.g. via the second system communication interface, to read or receive the data from the auxiliary memory of the second auxiliary component and store the data at the external memory.

The auxiliary components may be disinfected. For example, after transmitting the data to the auxiliary memory of the first auxiliary component, the second auxiliary component may be disinfected, e.g. after repositioning the second auxiliary component to a disinfection area. Thereby, the handling system may provide an additional functionality, and an operator may, e.g. after having preformed a procedure, provide the used auxiliary component at the handling system and be provided with a new disinfected auxiliary component now storing the data of the used auxiliary component. The handling system may comprise a disinfection area adapted to disinfect an auxiliary component positioned in the disinfection area, e.g. comprising a chamber wherein an auxiliary component may be subjected to ultraviolet radiation, heat, steam, gas and/or a disinfectant.

The handling system may be adapted to, after causing transmittal of the data from the auxiliary memory of the second auxiliary component to the auxiliary memory of the first auxiliary component, position the second auxiliary component in the disinfection area. Thereby, the second auxiliary component may be disinfected for the next time there is a need to swap an auxiliary component.

The handling system may comprise a conveyor, such as a conveyor belt, for repositioning the auxiliary components, e.g. from a receiving position, where the auxiliary components are received, to a retrieval position, where the auxiliary components after transfer of the data, is provided for retrieval by the user. The conveyor may further reposition the auxiliary components to the disinfection area, e.g. between the receiving position and the retrieval position.

A third auxiliary component may be received, e.g. at the handling system. The third auxiliary component may be received after providing the first auxiliary component for retrieval. Alternatively, the third auxiliary component may be received after receiving the first auxiliary component and before receiving the second auxiliary component, i.e. the third auxiliary component may be an intermediately received auxiliary component.

The rechargeable battery of the third auxiliary component may be charged, e.g. by a third system charging circuit of the handling system, or by the first system charging circuit or the second system charging circuit.

The data from the auxiliary memory of the third auxiliary component may be transmitted to the auxiliary memory of the second auxiliary component. The second auxiliary component may be provided for retrieval, e.g. after transmitting the data from the auxiliary memory of the third auxiliary component to the auxiliary memory of the second auxiliary component.

Various exemplary embodiments and details are described hereinafter, with reference to the FIGS. when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1a schematically illustrates an exemplary medical visualisation system 2 comprising an exemplary medical visualisation device 100 and an exemplary monitor device 200. In the illustrated example, the medical visualisation device 100 is an endoscope, such as a bronchoscope. In other examples, the medical visualisation device of the medical visualisation system may be a laryngoscope, a gastro-intestinal endoscope, a urology endoscope, etc.

The medical visualisation device 100 comprises a handle 118, and, in the illustrated example, the medical visualisation device 100 comprises an insertion tube 120 extending from the handle 118 to a distal tube portion 122. The handle may, as illustrated, comprise a control button 124 and the insertion tube 120 may comprise a bendable section 126.

The control button 124 is adapted to receive an input in a first input direction 125A and in a second input direction 126B. The bendable section 126 is adapted to bend accordingly in a first bending direction 128A and a second bending direction 128B. A touch input in the first input direction 125A causes the bendable section 126 to bend in the first bending direction 128A. A touch input in the second input direction 125B causes the bendable section 126 to bend in the second bending direction 128B.

The medical visualisation device 100 has an image sensor adapted to generate image data indicative of a view 114 from the visualisation device. As illustrated, the view 114 from the visualisation device 100 may be from the distal tube portion 122 of the insertion tube 120. The medical visualisation device 100 further comprises a light emitter adapted to provide illumination of the view 114.

The medical visualisation device 100 and the monitor device 200 are adapted to communicate wirelessly. For example, the medical visualisation device 100 is adapted to transmit image data using a downstream data channel from the medical visualisation device 100 to the monitor device 200. Alternatively or additionally, the medical visualisation device may be adapted to receive settings data using an upstream data channel from the monitor device 200 to the medical visualisation device 100.

The monitor device 200 comprises a first housing 202. In the illustrated example, the monitor device 200 further comprises a display 204 accommodated in the first housing 202. In alternative examples, the monitor device 200, such as the first housing 202 of the monitor device 200, may be coupled to an external display (see FIG. 1*b*). The monitor device 200 is operable to receive image data from a medical visualisation device 100 and display on the display a live representation of the image data indicative of the view 114 from the visualisation device 100. The display 204 may be a touch sensitive display.

The monitor device 200 may be adapted to wirelessly communicate with the medical visualisation device 100. For example, the monitor device 200 may be adapted to receive image data using the downstream data channel from the medical visualisation device 100 to the monitor device 200. The monitor device 200 may further be adapted to transmit settings data using an upstream data channel from the monitor device 200 to the medical visualisation device 100. Such settings data may, for example, be used to adjust brightness of the light emitter or control colour, contrast, gain and/or exposure settings of the image sensor. These settings may be adaptively adjusted based on the received image data, e.g. to adjust under/over exposure or similar.

The medical visualisation system 2 may be operable to store an image data file and/or a video sequence file in response to receipt of a user input signal indicative of a user activating an image capture button 119, 212. The image capture button may be a device button 119 on the medical visualisation device 100, and/or a monitor button 212 on the monitor device 200, e.g. a soft button displayed on the display 204.

Figure 1B:
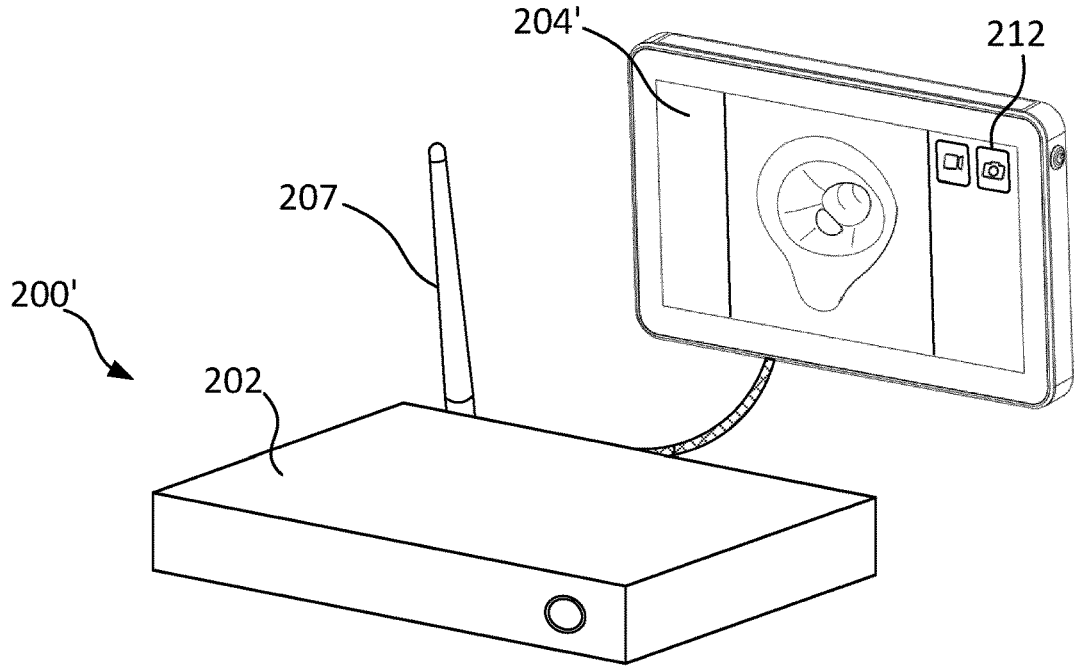

FIG. 1*b* schematically illustrates a monitor device 200' comprising a first housing 202, wherein the monitor device 200, such as the first housing 202, may be coupled to an external display 204'. The external display 204' may be a touch sensitive display. Other than the display 204' being external to the first housing 202, the monitor device 200' may be similar and comprise the same functionality as the monitor device 200. For example, the monitor device 200' is operable to receive image data from a medical visualisation device 100 (FIG. 1*a*) and display on the display 204' a live representation of the image data indicative of the view 114 from the visualisation device 100.

The monitor device 200' may be adapted to wirelessly communicate with the medical visualisation device 100. For example, the monitor device 200' may be adapted to receive image data using the downstream data channel from the medical visualisation device 100 to the monitor device 200'. The monitor device 200' may further be adapted to transmit settings data using an upstream data channel from the monitor device 200' to the medical visualisation device 100.

It is emphasized that the monitor device 200, as illustrated in the following examples may be substituted by the monitor device 200', as illustrated in FIG. 1*b*.

Figure 2:
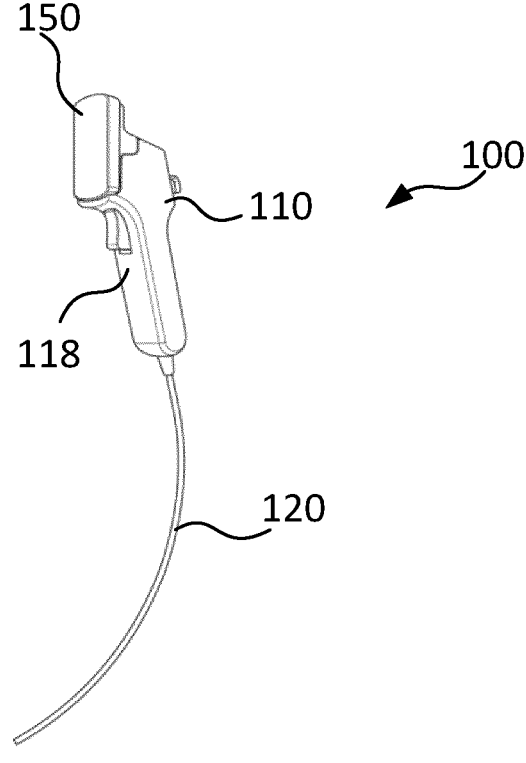
FIG. 2 schematically illustrates an exemplary medical visualisation device.

FIG. 2 schematically illustrates an exemplary medical visualisation device 100, such as the medical visualisation device 100 as described with respect to FIG. 1*a*.

The medical visualisation device 100 of FIG. 2 further comprises an auxiliary component 150 couplable to a main device part 110 of the medical visualisation device 100. The main device part 110 comprises the handle 118 and the insertion tube 120, as described with respect to FIG. 1*a*. The auxiliary component 150 comprises various electronic components, e.g. for establishing wireless communication with the monitor device.

The auxiliary component 150 may be adapted to be used multiple times, e.g. being reusable, while the man device part 110 may be configured as a single-use product, e.g. being disposable. By providing electronic components in a reusable component while the main device part being in direct contact with the patient being disposable, valuable resources may be preserved and costs may be lowered, while observing increased patient safety and reduced risk of cross contamination.

Figure 3A:
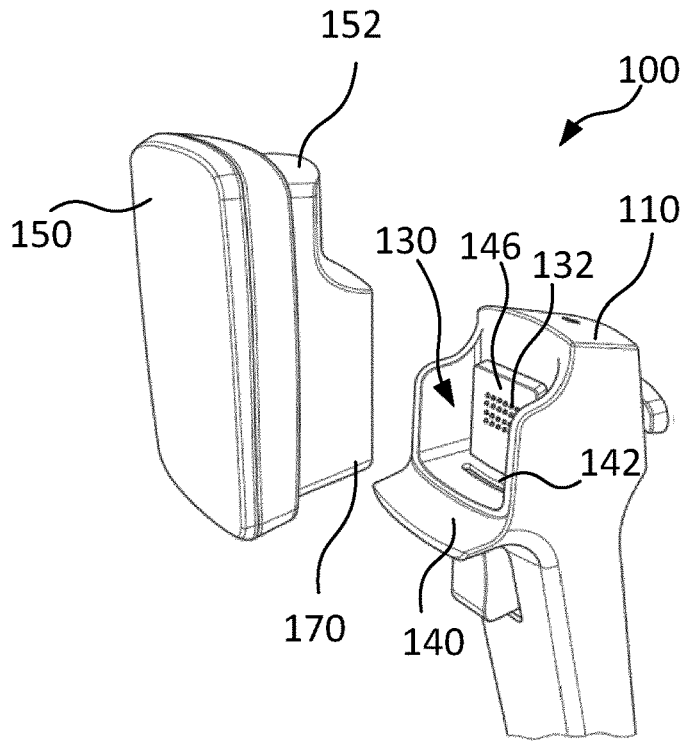
FIGS. 3*a* and 3*b* schematically illustrate the medical visualisation device.
Figure 3B:
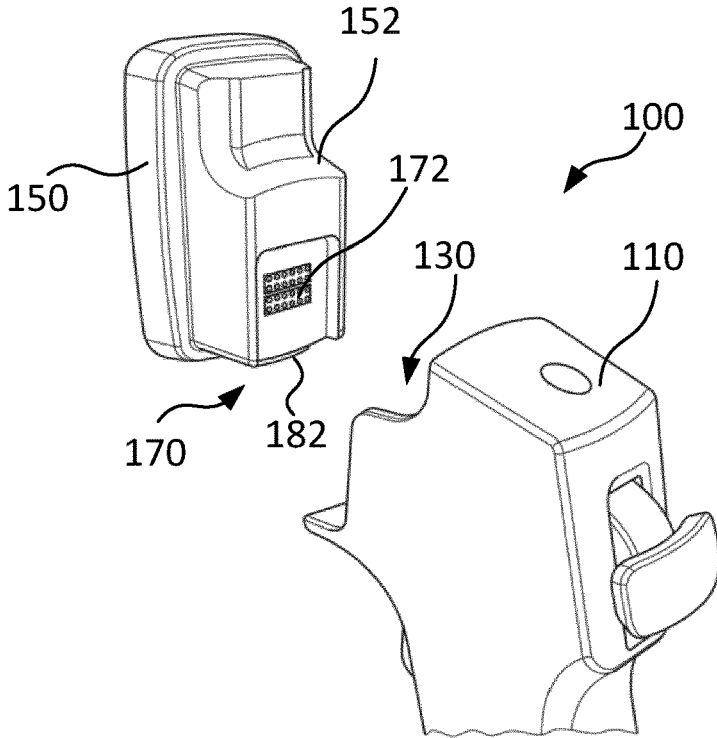

FIGS. 3*a* and 3*b* schematically illustrate the medical visualisation device 100, as also illustrated in FIG. 2, wherein the auxiliary component 150 is detached from the main device part 110.

The auxiliary component 150 comprises an auxiliary housing. The auxiliary housing 152 may be fluid-tight to the outside such that the auxiliary component 150 is adapted for wet cleaning, e.g. by immersion in a liquid. For example, the auxiliary housing 152 may be surface coated with a sealing liquid, e.g. by immersion in the sealing liquid, to make the auxiliary housing 152 fluid-tight. Alternatively or additionally, terminals of the auxiliary component 150 may be provided by insert moulding.

The main device part 110 comprises a main coupling part 130. The auxiliary component 150 comprises an auxiliary coupling part 170. The auxiliary coupling part 170 and the main coupling part 150 are adapted to be coupled. The main coupling part 130 is adapted to couple with the auxiliary coupling part 170. The auxiliary coupling part 170 is adapted to couple with the main coupling part 130.

The main coupling part 130 comprises one or more main terminals 132. The one or more main terminals 132 may be electrically connected to a light emitter and an image sensor of the main device part 110.

The auxiliary coupling part 170 comprises one or more auxiliary terminals 172. The one or more auxiliary terminals 172 and the one or more main terminals 132 are adapted to connect, when the auxiliary coupling part 170 is coupled with the main coupling part 130. The one or more auxiliary terminals 172 are adapted to connect to the one or more main terminals 132. The one or more main terminals 132 are adapted to connect to the one or more auxiliary terminals 172.

The main coupling part 130 has a main surface 140 with a main primary engagement member 142. The main primary engagement member 142 may be a recess, as illustrated. Alternatively, the main primary engagement member 142 may be a protrusion. The main primary engagement member 142 may be another suitable engagement member.

The auxiliary coupling part 170 has an auxiliary primary engagement member 182 adapted to engage with the main primary engagement member 142, such as to restrict movement of the auxiliary primary engagement member 182 along the main surface 140. For example, the auxiliary primary engagement member 182 may be a cooperating member of the main primary engagement member 142. For example, the auxiliary primary engagement member 182 may be a protrusion, as illustrated. Alternatively, the auxiliary primary engagement member 182 may be a recess. The auxiliary primary engagement member 182 may be another suitable engagement member.

The main coupling part 130 comprise a primary surface 146. The primary surface 146 accommodates exposed portions of the one or more main terminals 132. The primary surface 146 may be substantially perpendicular to the main surface 140, as illustrated.

The main coupling part 130 may have a main secondary engagement member, and the auxiliary coupling part may have an auxiliary secondary engagement member adapted to engage with the main secondary engagement member, such as to restrict movement of the auxiliary secondary engagement member perpendicular to the main surface 140. The primary surface 146 may be between the main primary engagement member 142 and the main secondary engagement member.

Figure 4:
FIG. 4 is a block diagram schematically illustrating a medical visualisation system, FIG. 5 schematically illustrates an exemplary operating room.

FIG. 4 is a block diagram schematically illustrating a medical visualisation system 2, such as the medical visualisation system 2 as described with respect to previous figures.

The medical visualisation system 2 comprises an exemplary medical visualisation device 100, such as the medical visualisation device 100 as described with respect to previous figures, and an exemplary monitor device 200, such as the monitor device 200 as described with respect to previous figures.

The medical visualisation device 100, as the medical visualisation device 100 of FIGS. 2 and 3, comprises a main device part 110 and an auxiliary component 150 couplable to the main device part 110.

The main device part 110 comprises an image sensor 112 adapted to generate image data indicative of a view from the main device part 110, a light emitter 116 adapted to provide illumination of the view, and a main coupling part 130 having one or more main terminals 132 electrically connected to the light emitter 116 and the image sensor 112. The main device part 110 may further comprise a safety circuit 134 and a device identifier 136.

The device identifier 136 may comprise device identifier information, such as serial number of the main device part 110, which may uniquely identify the main device part 110. Also, the device identifier information may be indicative of the type of visualisation device, e.g. whether the medical visualisation device 100 and/or the main device part 110 is a bronchoscope or a laryngoscope. Alternatively or additionally, the device identifier information may be indicative of the brand of the visualisation device, production version, batch number etc.

The device identifier 136 may include an electronically readable memory, such as an EPROM, RFID, NFC or similar. In other examples the device identifier may be a QR-code, bar-code or similar. The device identifier 136 may be connected to the one or more main terminals 132, as illustrated. However, in other exemplary medical visualisation devices, the device identifier 136 may be readable without the necessity to establish an electrical contact. For example, the device identifier 136 may be readable by means of a short-range communication circuit, such as an RFID or NFC circuit. In other exemplary medical visualisation devices, the device identifier 136 may be optically read, e.g. wherein the device identifier is a QR-code or bar code.

The auxiliary component 150 comprises an auxiliary coupling part 170 adapted to couple with the main coupling part 130. The auxiliary coupling part 170 comprises one or more auxiliary terminals 172 adapted to connect to the one or more main terminals 132 of the main coupling part 130, when the auxiliary coupling part 170 is coupled with the main coupling part 130.

The auxiliary component 150 comprises a device processing unit 154 and a device wireless communication module 156. The auxiliary component 150 may further comprise an auxiliary memory 155, such as a flash memory or other suitable electronic memory. The device processing unit 154 may be adapted to read and/or write to/from the auxiliary memory 155. The auxiliary component 150 may further comprise a battery 160, as illustrated. The battery 160 may be a rechargeable battery.

The device processing unit 154 is electrically connected to the one or more auxiliary terminals 172 and adapted to receive the image data from the image sensor 112, when the auxiliary component 150 is coupled to the main device part 110. The device processing unit 154 may further be adapted to encode the image data to provide encoded image data based on the image data, and transmit the image data and/or the encoded image data to the device wireless communication module 156, for wireless transmission to the monitor device 200. For example, the device processing unit 154 may encode the image data in accordance with a wireless video transmission protocol.

The device wireless communication module 156 is connected to the device processing unit 154 and adapted to communicate with a monitor wireless communication module 206 of the monitor device 200. The device wireless communication module 156 is adapted to receive the image data and/or the encoded image data from the device processing unit 154 and transmit the image data and/or the encoded image data using a downstream data channel 4 to the monitor wireless communication module.

The device processing 154 unit may be adapted to obtain the device identifier information from the device identifier 136, e.g. via the one or more auxiliary terminals 172 and one or more main terminals 132.

The battery 160 is adapted to power the medical visualisation device 100. The battery 160 is adapted to power the electronic elements of the auxiliary component 150, such as the device processing unit 154 and/or the device wireless communication module. For example, the battery 160 may be connected to the electronic components of the auxiliary component 150, e.g. the device processing unit 154 and/or the device wireless communication module. The battery 160 is electrically connected to the one or more auxiliary terminals 172, such as to power the main device part 110 and/or the electronic elements thereof, when the auxiliary component 150 is coupled to the main device part 110, such as when the main coupling part 130 is coupled with the auxiliary coupling part 170. For example, the battery 160 may be adapted to power the image sensor 112 and light emitter 114 of the main device part 110. The battery 160 may be adapted to power the device identifier 136.

The safety circuit 134 may be adapted to prevent excessive current to the elements of the main device part 110, such as the light emitter 116, the image sensor 112 and/or the device identifier 136. For example, the one or more main terminals 132 may be electrically connected to the light emitter 116, the image sensor 112 and/or the device identifier 136 via the safety circuit. Thereby, the elements of the main device part 110 may be protected, in case an auxiliary component able to power another, more power consumptive, device part, is coupled to the main device part 110.

The monitor device 200 comprises the monitor wireless communication module 206 and a monitor processing unit 208. The monitor device 200 may comprise a monitor memory 210, such as a Flash memory or other suitable electronic memory.

The monitor device 200 may further comprise a display 204, as illustrated. In an alternative example, such as exemplified for the monitor device 200' in FIG. 1*b*, the monitor device may be couplable to an external display. In either case, the display 204 may be operable to display a live representation of the image data indicative of the view 114 from the visualisation device 100. The display 204 may be touch sensitive display.

The monitor wireless communication module 206 is adapted to communicate with the device wireless communication module 156. The monitor wireless communication module 206 is adapted to receive image data and/or encoded image data using the downstream data channel 4 from the device wireless communication module 156 to the monitor wireless communication module 206. The monitor wireless communication module 206 may further be adapted to transmit the received image data and/or encoded image data to the monitor processing unit 208.

The monitor processing unit 208 is adapted to receive the image data and/or the encoded image data from the monitor wireless communication module 206. The monitor processing unit 208 may further be adapted to decode the encoded image data. The monitor processing unit 208 may be adapted to cause the display 204 to display a live representation of the image data.

The monitor wireless communication module 206 may further be adapted to transmit settings data using an upstream data channel 6 from the monitor wireless communication module 206 to the device wireless communication module 156. The device wireless communication module 156 is adapted to receive settings data using the upstream data channel 6.

The monitor processing unit 208 may be adapted to generate and/or provide the settings data to the monitor wireless communication module 206 for transmission to the medical visualisation device. For example, the monitor processing unit 208 may generate the settings data based on the image data, e.g. to adjust settings of one or more components of the medical visualisation device 100, e.g. the light emitter 116 and/or the image sensor 112. The device processing unit 154 may be adapted to receive the settings data from the device wireless communication module 156 and adjust settings of one or more components of the medical visualisation device 100 based on the settings data. For example, the settings data may be indicative of adjustment of the image sensor, e.g. including colour, contrast, gain, and/or exposure settings. Alternatively or additionally, the settings data may be indicative of adjustment of the light emitter, e.g. including current, brightness, and/or PWM settings. By utilizing the upstream data channel 6 to transmit settings data, the monitor processing unit 208 may process the image data received and continuously adjust settings of the light emitter 116 and/or image sensor 112, to enhance the image quality. Thereby, the heavier computational image analysis may be performed in the monitor device 200, allowing the medical visualisation device 100 to draw less power, needing less battery capacity and effectively allowing the medical visualisation device to be lighter and more compact.

The wireless communication between the medical visualisation device 100 and the monitor device 200 may be established by activation of a pairing sequence, e.g. by the user pressing a pairing button on the monitor device 200 and on the medical visualisation device 100. In response to activation of the pairing sequence, the device processing unit 154 and the monitor processing unit 208 cause the device wireless communication module 156 and the monitor wireless communication module 206 to exchange information to setup a data link for subsequent data transfer, e.g. including information regarding communication channel for the data link, identification details of the respective devices, etc.

After establishing the data link, an initialisation sequence may be performed. Alternatively, the initialisation sequence may be performed in response to the auxiliary component 150 and the main device part 110 being coupled. The initialisation sequence may include that the monitor processing unit 208 receives device identifier information from the device identifier 136. Based on the device identifier information, the monitor processing unit 208 is able to process the image data received from the medical visualisation device 100. Based on the device identifier information, the monitor processing unit 208 may generate and/or provide initial settings data to the monitor wireless communication module 206 for transmission to the medical visualisation device 100, such as to the device processing unit 154, which may adjust settings of one or more components of the medical visualisation device 100 based on the initial settings data. Thereby, the settings of the one or more components may be set to a default or initial value, which may be dependent on various information related to the specific device, i.e. based on the device identifier information. Similar to the settings data, explained above, the initial settings data may be indicative of adjustment of the image sensor, e.g. including colour, contrast, gain, and/or exposure settings. Alternatively or additionally, the initial settings data, like the settings data, may be indicative of adjustment of the light emitter, e.g. including current, brightness, and/or PWM settings.

The initialisation sequence may further include that a designated user interface is loaded on the monitor device 200. For example, a designated user interface may be loaded based on the device identifier information, e.g. depending on whether the medical visualisation device 100 and/or the main device part 110 is a bronchoscope, a laryngoscope, or another visualisation device.

Further, FIG. 4 also illustrates that the medical visualisation system 2 may comprise a plurality of medical visualisation devices, e.g. the first medical visualisation device 100 as already described and a second medical visualisation device 100'. The second medical visualisation device 100' may generally comprise the similar features and components as the first medical visualisation device 100 and is therefore, for brevity, not described in further details. As seen the monitor device 200, such as the monitor wireless communication module 206 may be adapted to communicate with the second medical visualisation device 100', such as with a device wireless communication module of the second medical visualisation device 100'. For example, the monitor wireless communication module 206 may be adapted to receive image data and/or encoded image data using a downstream data channel from the second medical visualisation device 100'. The monitor processing unit 208 may be adapted to cause the display 204 to display a live representation of the image data of the second medical visualisation device 100', e.g. simultaneously with display of the image data of the first medical visualisation device 100, e.g. side by side or picture-in-picture, or in another arrangement.

The monitor wireless communication module 206 may further be adapted to transmit settings data using an upstream data channel from the monitor wireless communication module 206 to the second medical visualisation device 100', such as to a device wireless communication module of the second medical visualisation device, as similarly described with respect to the medical visualisation device 100.

Figure 5:
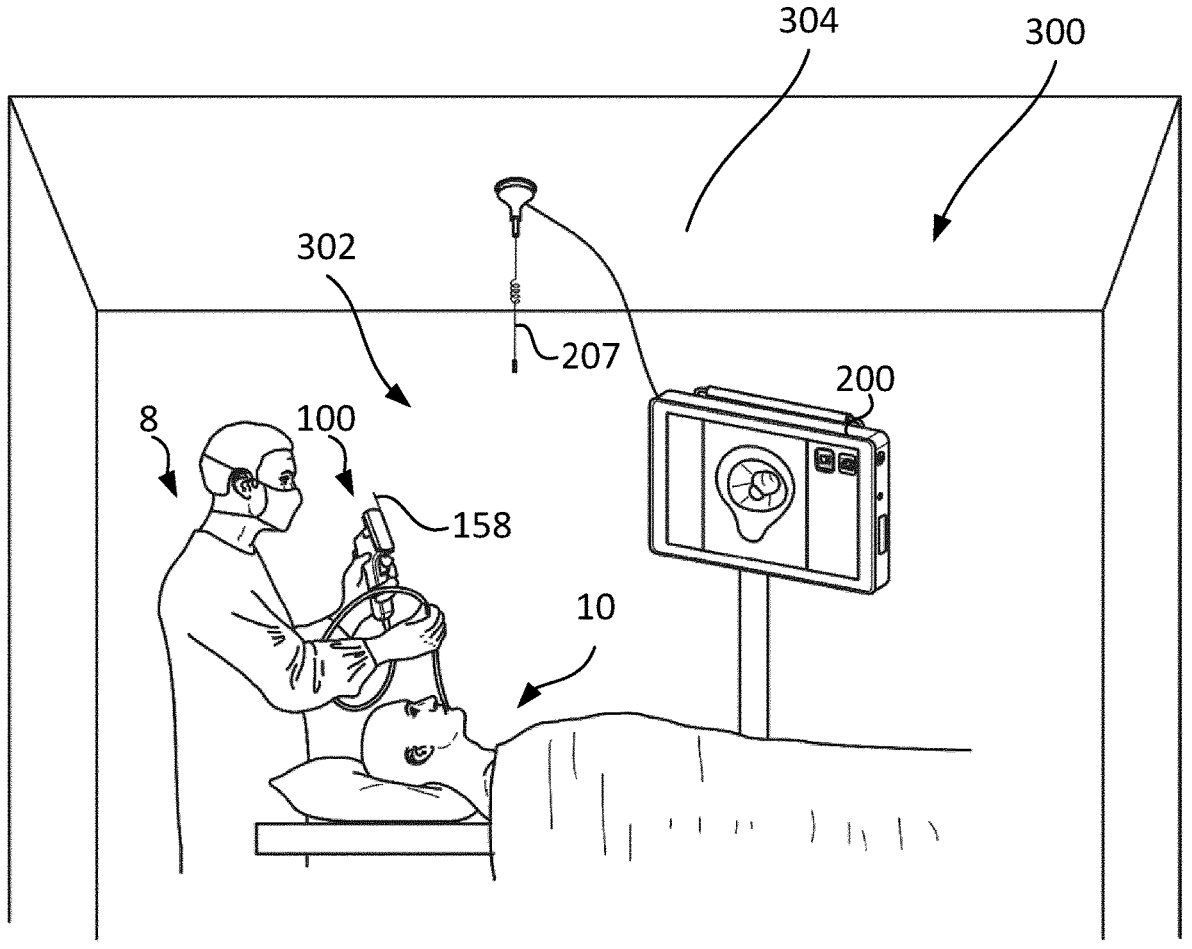

FIG. 5 schematically illustrates an exemplary operating room 300 with an operating setting 302, wherein an endoscope procedure is being performed on a patient 10 by an operator 8 of a medical visualisation device 100. The operator 8 is seeing the view from the medical visualisation device 100 at the monitor device 200.

The monitor wireless communication module of the monitor device 200 comprises a monitor antenna 207, and the device wireless communication module of the medical visualisation device 100 comprises a device antenna 158. Here the device antenna 158 is shown for the purpose of illustration, alternatively, the device antenna 158 may be positioned inside a housing of the medical visualisation device 100.

The image data from the medical visualisation device 100 is transmitted to the monitor device by wireless communication via the device antenna 158 and the monitor antenna 207. To ensure constant wireless transfer of the image data, it may be advantageous to ensure or promote line of sight between the device antenna 158 and the monitor antenna 207. Therefore, the monitor antenna 207 is positioned external to a housing of the monitor 200. The monitor antenna 207 may be positioned at a distance from the housing, e.g. of more than 2 meters. The monitor antenna 207 may be adapted to be positioned above the operating setting 302, such as at the ceiling 304 of the operating room 300, as illustrated.

Figure 6:
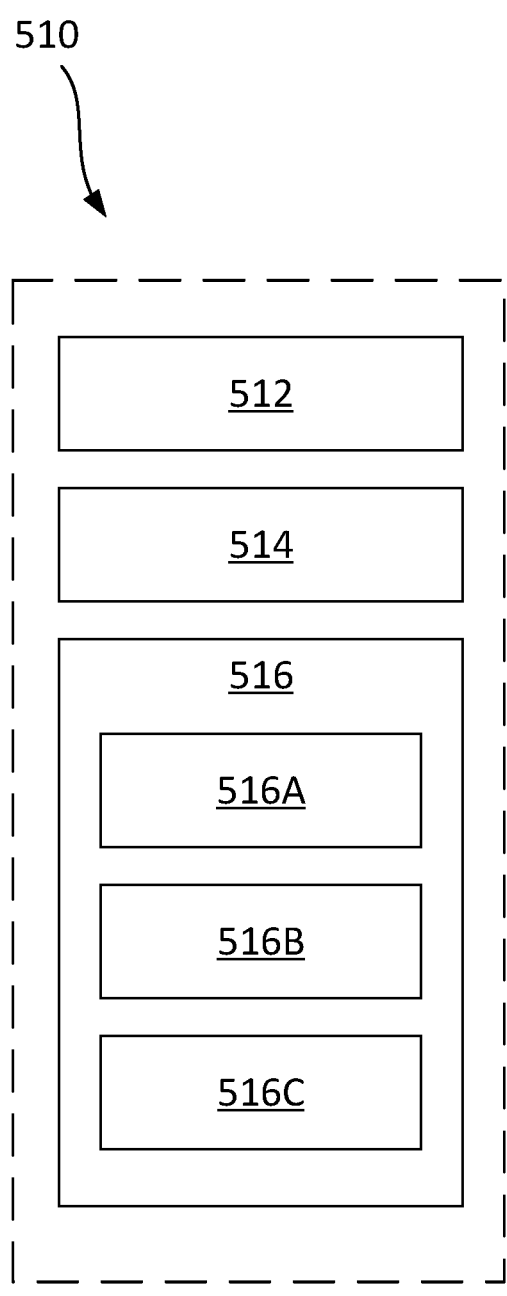
FIG. 6 is a block diagram schematically illustrating exemplary initial data.

FIG. 6 is a block diagram schematically illustrating exemplary initial data 510 of the auxiliary memory. The auxiliary memory 155 of the auxiliary component 150 (cf. FIG. 3) may store initial data 510 for being loaded by the monitor device. For example, the initial data 510 may be loaded by the monitor device upon initialisation of a new procedure, e.g. upon establishing connection between the auxiliary component and the monitor device. The auxiliary component may be enablable to transmit the initial data to the monitor device, e.g. using an auxiliary communication interface. The monitor processing unit may be adapted to receive the initial data 510 and adjust one or more parameters of the medical visualisation system based on the initial data 510.

For example, the initial data 510 may comprise patient data 512, e.g. of the patient on which the procedure is about to be performed. Thus, the monitor device may retrieve and store patient data from the auxiliary component. For example, the auxiliary component may be adapted to follow the patient, and upon performing a procedure, by using the "personal" auxiliary component of the patient, the correct data of the patient is automatically received by the monitor device, and the monitor device may be adapted to associate the patient data with the image data, such as any stored still images or video sequences. The patient data 512 may include patient name, social security number, etc. The patient data 512 may also include information about the procedure to be performed, medical history, information about allergies, etc. Thereby, all relevant information may be right at hand for the operator of the medical visualisation system.

Alternatively or additionally, the initial data 510 may comprise operator data 514 indicative of the operator performing the medical visualisation procedure. Thus, the monitor device may retrieve and store operator data from the auxiliary component, such as to log information about the operator performing the procedure. For example, the auxiliary component may be adapted to follow the operator, and upon performing a procedure, by using the "personal" auxiliary component of the operator, the data of the operator is automatically received by the monitor device, and the monitor device may be adapted to associate the operator data with the image data, such as any stored still images or video sequences.

The auxiliary memory may also work as a storage device for storing image data files and/or video sequence files. Thus, the monitor processing unit and/or the device processing unit may store an image data file and/or video sequence file in the auxiliary memory in response to receipt of a user input signal indicative of a user activating an image capture button, as described above in relation to FIG. 1*a*. In accordance with the above, the monitor processing unit and/or the device processing unit may be adapted to associate the patient data and/or the operator data with the image data file. Thereby, the files stored during the procedure may be conveniently stored in the auxiliary component and follow either the patient or the operator for later retrieval.

Alternatively or additionally. The initial data 510 may comprises operator setup data 516 associated with the operator performing the medical visualisation procedure. Thus, this may be particularly useful when the initial data 510 also comprises operator data 514.

The operator setup data 516 may include image parameters 516A, e.g. including settings for hue, saturation, brightness, contrast, and/or sharpness. The monitor processing unit may, in response to receiving the initial data 510, adjusts image parameters of the live representation of the image data displayed on the display in accordance with the image parameters 516A of the operator setup data 516. Thus, the system may conveniently adjust parameters to be in accordance with preferences of the operator, thereby reducing unnecessary time to setup the monitor device in accordance with individual preferences of an operator.

The medical visualisation system, such as the monitor device and/or the medical visualisation device may, as previously described, comprise one or more buttons adapted to receive user inputs. The operator setup data 516 may include button settings 516B indicative of functions assigned to one or more of the buttons, e.g. on the handle of the main device part or on the monitor device. The monitor processing unit may, in response to receiving the initial data 510, assign functions to the one or more of the buttons in accordance with the button settings 516B of the operator setup data 516. Thus, the system may conveniently setup the devices in accordance with preferences of the operator, thereby reducing unnecessary manual setup time prior to a procedure.

The monitor processing unit and/or the device processing unit may be adapted to perform tasks based on spoken inputs. Thus, the operator setup data 516 may include voice control data 516C associated with the operator, e.g. including keywords, training data etc. The monitor processing unit, after receiving the initial data 510, may identify tasks to be performed based on the spoken inputs and the voice control data 516C of the initial data 516.

The monitor processing unit may be adapted to store new operator setup data 516, and/or to update the currently stored operator setup data 516 in the auxiliary memory based on a current set of settings of the monitor device. For example, the monitor processing unit may store or update operator setup data in the auxiliary memory in response to receipt of a user input signal indicative of a user requesting storing of the current set of settings. For example, a designated button may be provided, or a certain input, e.g. pressing a predetermined button for more than a predetermined time, may activate a storing/updating procedure of the operator setup data 516.

Figure 7:
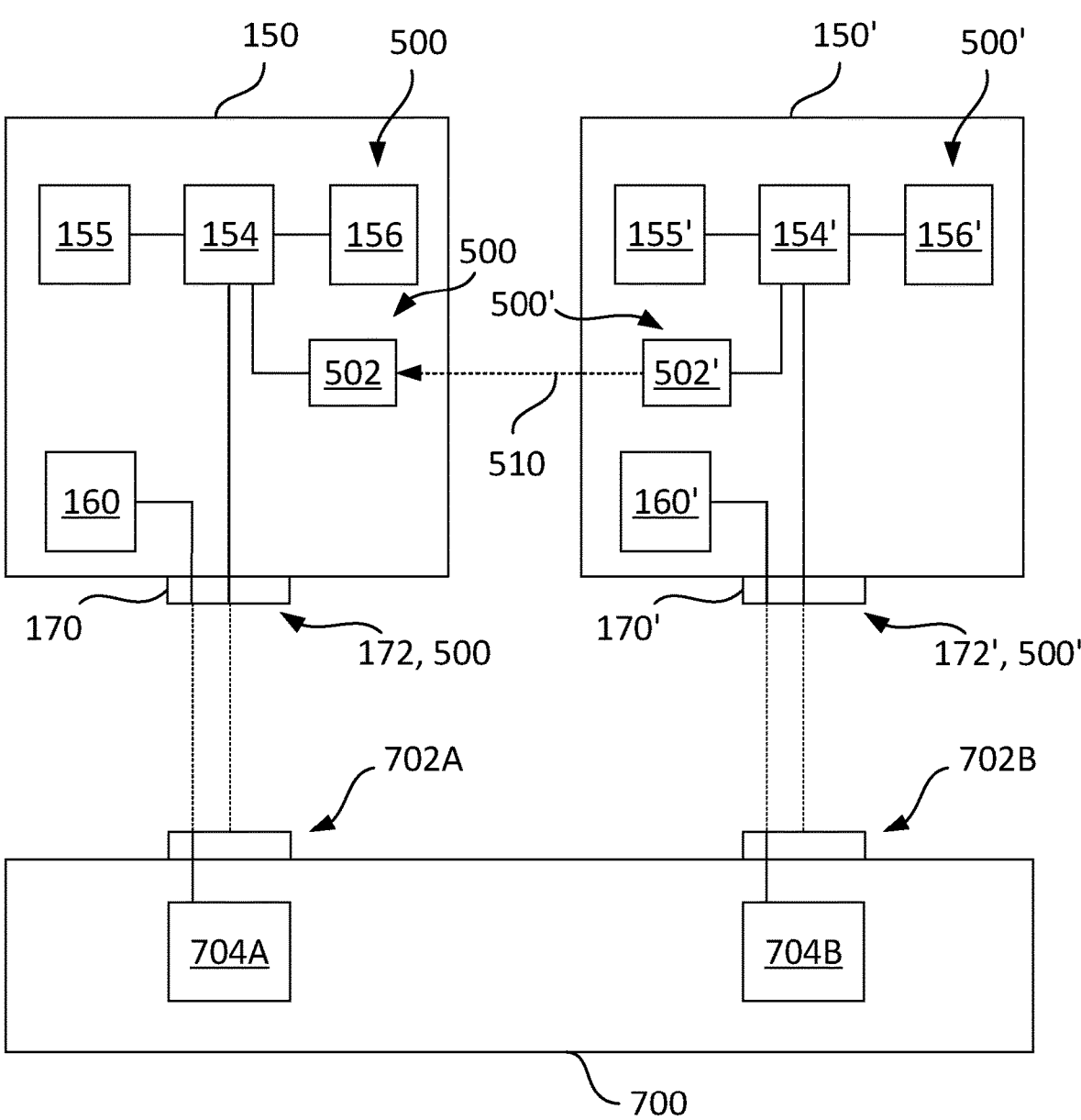
FIG. 7 is a block diagram schematically illustrating an exemplary handling system and exemplary auxiliary components.

FIG. 7 is a block diagram schematically illustrating an exemplary handling system 700 and exemplary auxiliary components 150, 150', such as the auxiliary component as described in relation to the previous figures, i.e. each auxiliary component 150, 150' is adapted to be coupled to a respective main device part (e.g. the main device part 110 as illustrated in FIGS. 2-4. The handling system 700 is configured for handling the auxiliary components. The auxiliary components include a first auxiliary component 150 and a second auxiliary component 150'.

The auxiliary components 150, 150' each comprises a rechargeable battery 160, 160' adapted to power electronic components of the auxiliary component 150, 150' and of the respective main device part, i.e. of the main device part to which it is coupled. Each auxiliary component 150, 150' further comprises an auxiliary memory 155 and one or more auxiliary communication interface 500, 500'. In the illustrated example of FIG. 7, the auxiliary components 150, 150' each comprises a plurality of auxiliary communication interfaces 500, 500' including the device wireless communication module 156, 156' and the auxiliary terminals 172, 172' of the auxiliary coupling part 170, 170', as described with respect to FIG. 3. Furthermore, as illustrated, the auxiliary components 150, 150', e.g. as an auxiliary communication interface 500, 500', may comprise a short-range communication circuit 502, 502'. The short-range communication circuits 502, 502' may be contactless, e.g. inductive, communication circuits, e.g. using near field communication (NFC), Bluetooth or similar technology. The auxiliary components 150, 150' may further comprise a device processing unit 154, 154' as previously described.

The handling system 700 comprises a first system communication interface 702A adapted to couple with the auxiliary communication interface 500 of the first auxiliary component 150, e.g. with the auxiliary terminals 172 of the first auxiliary component 150. The handling system 700 comprises a second system communication interface 702B adapted to couple with the auxiliary communication interface 500' of the second auxiliary component 150', e.g. with the auxiliary terminals 172' of the second auxiliary component 150'.

The handling system is adapted to, via the first system communication interface 702A and/or the second system communication interface 702B, to cause transmittal of data, e.g. the initial data 510 as described in relation to FIG. 6, from the auxiliary memory 155' of the second auxiliary component 150' to the auxiliary memory 155 of the first auxiliary component 150. For example, a system processing unit (not illustrated) of the handling system 700 may be adapted to cause transmittal of the data 510. Alternatively, the system communication interfaces 702A, 702B may comprise wiring of terminals which upon coupling with the auxiliary components 150, 150' activate a procedure in the auxiliary components 150, 150' to transmit the data 510. As illustrated, the data 510 may be transmitted by wireless communication between the short-range communication circuit 502 of the first auxiliary component 150 and the short-range communication circuit 502' of the second auxiliary component 150.

The handling system 700 further comprises a system charging circuit 704A, 704B adapted to charge the rechargeable battery 160 of the first auxiliary component 150 and/or the rechargeable battery 160' of the second auxiliary component 150'. In the illustrated example, the handling system 700 comprises a first system charging circuit 704A adapted to charge the rechargeable battery 160 of the first auxiliary component 150 and a second system charging circuit 704B adapted to charge the rechargeable battery 160' of the second auxiliary component 150'.

The handling system 700 may be adapted to validate the data 510 of the auxiliary memory 155 of the first auxiliary component 150 after transmittal of the data 510 to the auxiliary memory 155 of the first auxiliary component 150. Hence, the handling system 700 may make sure that the data 510 is correctly transmitted and stored in the auxiliary memory 155 of the first auxiliary component 150.

The handling system 700 may be adapted to delete the data 510 from the auxiliary memory 155' of the second auxiliary component 150' after transmittal of the data 510 to the auxiliary memory 155 of the first auxiliary component 150 and preferably after having validated the data 510 of the auxiliary memory 155 of the first auxiliary component 150.

Figure 8:
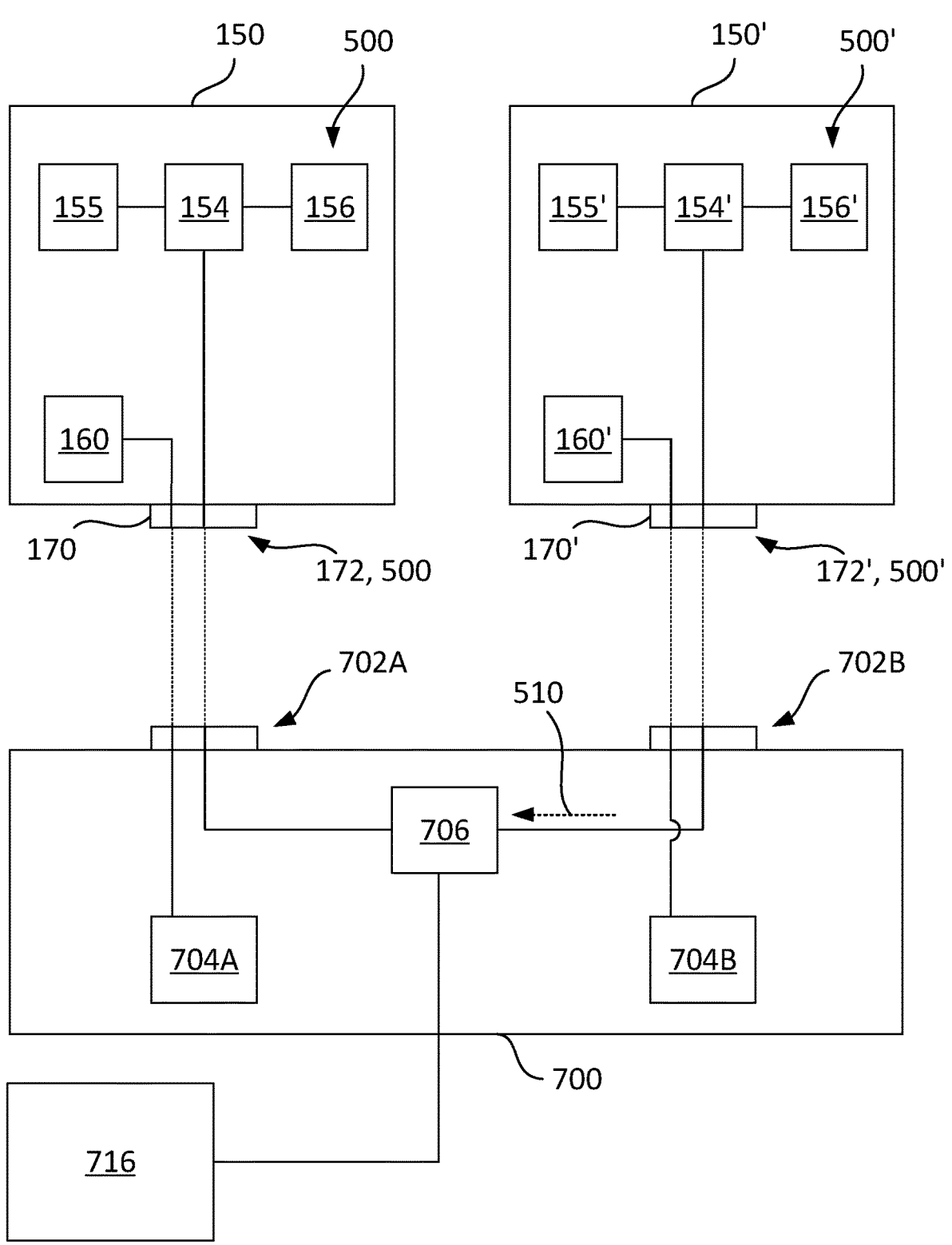
FIG. 8 is a block diagram schematically illustrating an exemplary handling system and exemplary auxiliary components, FIG. 9 schematically illustrates an exemplary handling system, FIG. 10 schematically illustrates an exemplary handling system, FIG. 11 schematically illustrates exemplary auxiliary components, FIGS. 12*a* and 12*b* each schematically illustrates an exemplary auxiliary component.

FIG. 8 is a block diagram schematically illustrating an exemplary handling system 700 and exemplary auxiliary components 150, 150', such as the auxiliary component as described in relation to the previous figures, i.e. each auxiliary component 150, 150' is adapted to be coupled to a respective main device part (e.g. the main device part 110 as illustrated in FIGS. 2-4. The handling system 700' is configured for handling the auxiliary components. The auxiliary components include a first auxiliary component 150 and a second auxiliary component 150'.

The auxiliary components 150, 150' are similar to the auxiliary components 150, 150' described and illustrated in relation to FIG. 7. However, as illustrated, the short-range communication circuits 502, 502' as illustrated in FIG. 7, may be omitted.

The handling system 700 is similar to the handling system 700 as described and illustrated in relation to FIG. 7. However, as illustrated, the handling system 700 may comprise a system processing unit 706 connected to the system communication interfaces 702A, 702B. Thus, in the example of FIG. 8, the handling system 700 transmits the data 510 from the auxiliary memory 155' of the second auxiliary component 150' to the auxiliary memory 155 of the first auxiliary component 150, by the system processing unit 706 being adapted to read or receive the data 510 of the auxiliary memory 155' of the second auxiliary component 150', e.g. via the second system communication interface 702B and optionally via the device processing unit 154' of the second auxiliary component 150', and to write or transmit the data 510 to the auxiliary memory 155 of the first auxiliary component 150, e.g. via the first system communication interface 702A and optionally via the device processing unit 154 of the first auxiliary component 150.

The handling system 700 may further be connectable to an external memory 716, e.g. at a server. The handling system 700, such as the system processing unit 706 of the handling system 700 may be adapted to store the data 510 at the external memory. For example, the external memory 716 may provide a backup in case data at an auxiliary component is corrupted or lost.

Figure 9:
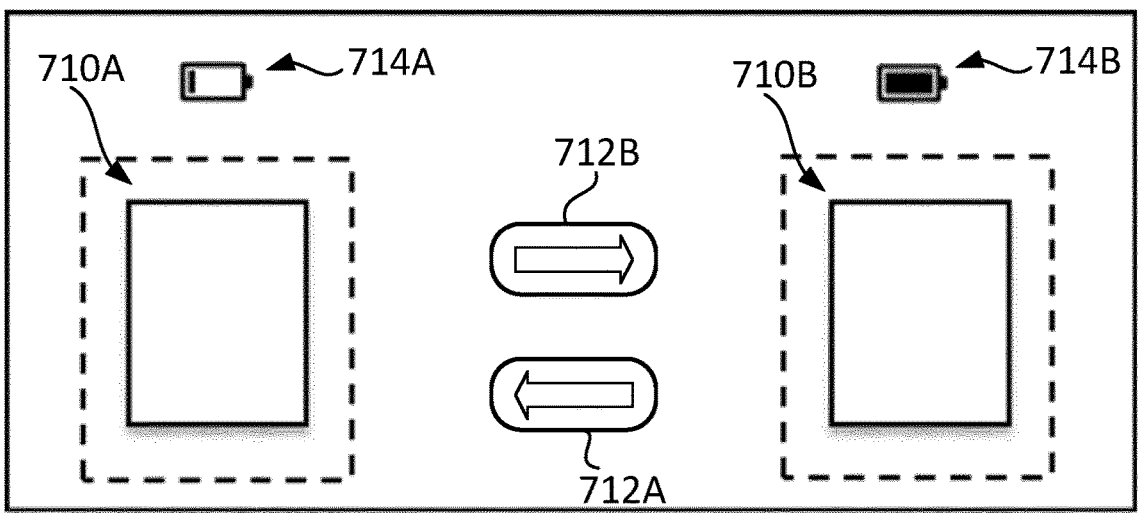

FIG. 9 schematically illustrates an exemplary handling system 700, such as the handling system as described in relation to FIGS. 7 and 8. The handling system 700 comprises a plurality of component positions 710A, 710B including a first component position 710A adapted to receive the first auxiliary component (not shown) and a second component position 710B adapted to receive the second auxiliary component (not shown). The component positions 710A, 710B may comprise terminals of the system communication interfaces 702A, 702B as described in relation to FIGS. 7 and 8.

The user may position a first auxiliary component in the first component position 710A and a second auxiliary component in the second component position 710B to have data transmitted from the second auxiliary component to the first auxiliary component and/or from the first auxiliary component to the second auxiliary component. In some exemplary handling systems 700 the data may be transmitted automatically after the user has positioned the auxiliary components, e.g. after a predetermined time, optionally after providing a visual or audible indication of data being transmitted, to allow the user a chance to cancel the transmittal, if it was not intended. In other exemplary handling systems 700, e.g. as illustrated, the handling system 700 may comprise one or more transmit buttons 712A, 712B, and be adapted to cause the transmittal of data upon a user pressing the first transmit button, e.g. for a predetermined amount of time, e.g. 3 seconds. For example, the handling system 700 may comprise a first transmit button 712A, and the handling system 700 may be adapted to cause the transmittal of data from the auxiliary memory of the second auxiliary component, i.e. the auxiliary component being positioned in the second component position 710B, to the auxiliary memory of the first auxiliary component, i.e. the auxiliary component being positioned in the first component position 710A, upon a user pressing the first transmit button 712A.

The handling system 700 may comprise a second transmit button 712B, and the handling system 700 may be adapted to cause the transmittal of data from the auxiliary memory of the first auxiliary component, i.e. the auxiliary component being positioned in the first component position 710A, to the auxiliary memory of the second auxiliary component, i.e. the auxiliary component being positioned in the second component position 710B, upon a user pressing the second transmit button 712B.

By providing both a first and a second transmit button 712A, 712B, the user may arbitrarily choose which of the auxiliary components should receive the data of the other auxiliary component.

The handling system 700 may further comprise one or more battery indicators 714A, 714B adapted to display a visual indication of estimated battery capacity of the rechargeable battery of the first auxiliary component and/or the second auxiliary component, i.e. the auxiliary component being positioned in the first component position 710A and/or the second component position 710B, respectively. For example, the handling system 700 comprises a first battery indicator 714A adapted to display a visual indication of estimated battery capacity of the rechargeable battery of the first auxiliary component, i.e. the auxiliary component being positioned in the first component position 710A. Furthermore, the handling system 700 comprises a second battery indicator 714B adapted to display a visual indication of estimated battery capacity of the rechargeable battery of the second auxiliary component, i.e. the auxiliary component being positioned in the second component position 710B.

Figure 10:
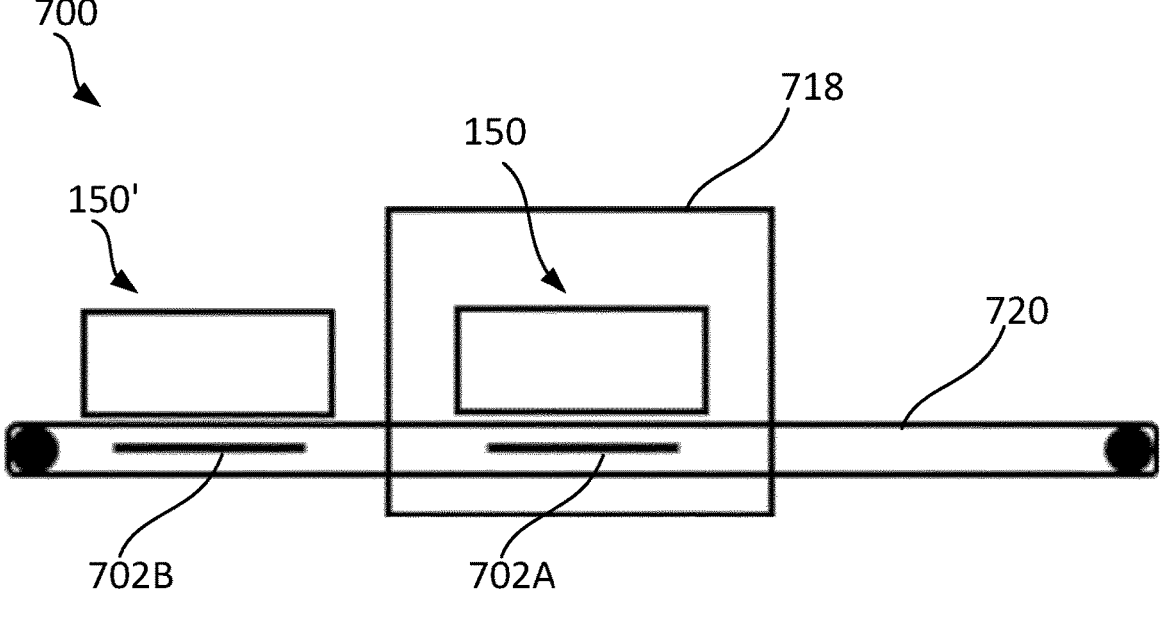

FIG. 10 schematically illustrates an exemplary handling system 700, such as the handling system as described in relation to FIGS. 7 and 8. The handling system 700 comprises a disinfection area 718 adapted to disinfect an auxiliary component positioned therein. For example, the disinfection area 718 may comprise a chamber wherein an auxiliary component is subjected to ultraviolet radiation, gas, heat, steam, and/or a disinfectant. The handling system 700 is adapted to, after causing transmittal of the data from the auxiliary memory of the second auxiliary component 150 to the auxiliary memory of the first auxiliary component 150', position the second auxiliary component in the disinfection area 718. Thus, a newly disinfected auxiliary component may be available for later receipt of data.

The handling system 700 may comprise a conveyor, such as a conveyor belt 720, as illustrated, for repositioning the auxiliary components 150, 150'. For example, the conveyor belt 720 may, e.g. after transferring the data from the second auxiliary component 150' to the first auxiliary component 150, move the second auxiliary component to the prior position of the first auxiliary component, e.g. above the first system communication interface 702A and/or within the disinfection area 718, and provide the first auxiliary component 150 for retrieval by the user on the opposite side of the disinfection area 718.

Figure 11:
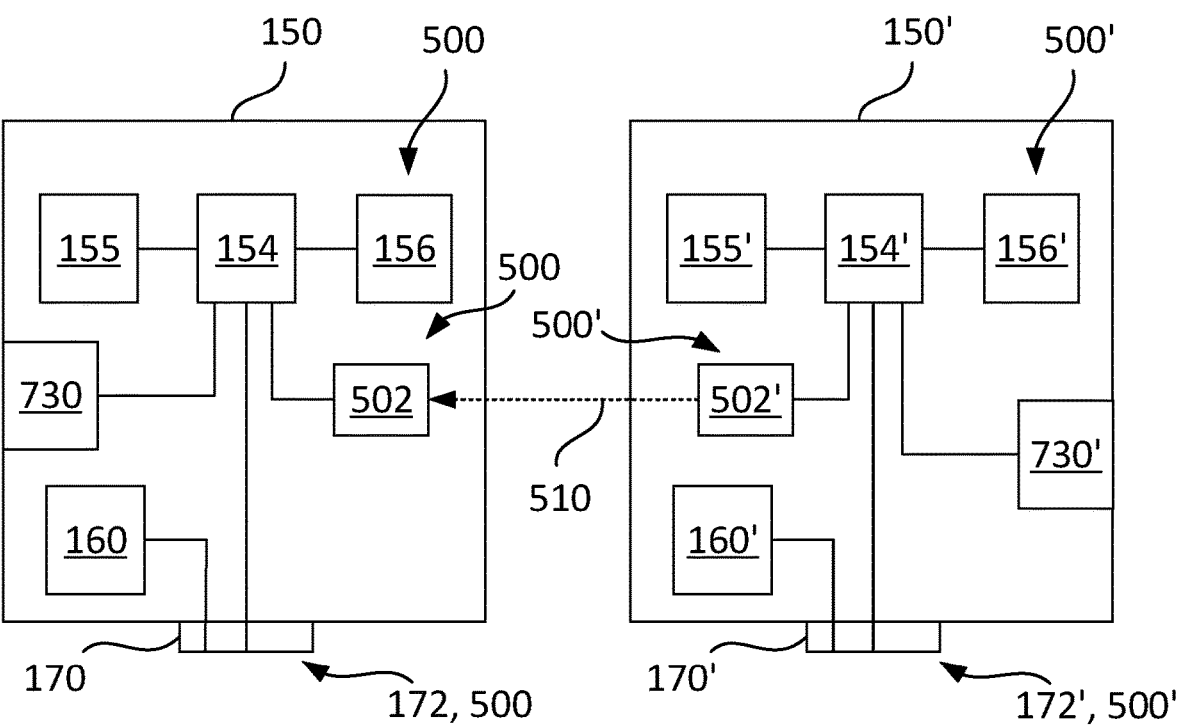

FIG. 11 schematically illustrates exemplary auxiliary components 150, 150', such as the auxiliary component as described in relation to the previous figures, i.e. each auxiliary component 150, 150' is adapted to be coupled to a respective main device part (e.g. the main device part 110 as illustrated in FIGS. 2-4. The auxiliary components 150, 150', as illustrated, may be able to transmit data 510 between them without the need for the handling system 700 as described in relation to the previous figures. The auxiliary components include a first auxiliary component 150 and a second auxiliary component 150'.

The auxiliary components 150, 150' each comprises an auxiliary memory 155, 155' and one or more auxiliary communication interface 500, 500' including short range communication circuits 502, 502'. The short-range communication circuits 502, 502' may be contactless, e.g. inductive, communication circuits, e.g. using near field communication (NFC), Bluetooth or similar technology. The auxiliary components 150, 150' may further each comprise a device processing unit 154, 154' as previously described. Furthermore, the auxiliary components 150, 150', as illustrated in FIG. 11, each may comprise an auxiliary user interface 730, 730'. The auxiliary user interface(s) may comprise a button, a touch screen or other suitable input devices.

The first auxiliary component 150 and the second auxiliary component 150' may be adapted to transmit, via the short range communication circuits 502, 502', data 510 from the auxiliary memory 155' of the second auxiliary component 150' to the auxiliary memory 155 of the first auxiliary component 150, in response to receiving, at the auxiliary user interface(s) 730, 730', one or more user inputs indicative of a request to transmit the data 510 from the auxiliary memory 155' of the second auxiliary component 150' to the auxiliary memory 155 of the first auxiliary component 150. For example, the one or more user inputs may comprise receiving a first user input at the auxiliary user interface 730 of the first auxiliary component 150 and while or after receiving the first user input at the auxiliary user interface

730 of the first auxiliary component 150 receiving a second user input at the auxiliary user interface 730' of the second auxiliary component 150. For example, the user may simultaneously press and hold a button on both auxiliary components 150, 150' to initiate transmission of data 510, a further input, e.g. on a second button, may indicate whether the data 510 should be transmitted from the first auxiliary component 150 to the second auxiliary component 150' or vice versa.

In a scenario where the battery of an auxiliary component, e.g. of the first auxiliary component 150 of FIG. 11, is too low to allow transfer of data. The user may need to recharge the auxiliary component or transfer the data using a handling system 700 as described in relation to the previous figures. The auxiliary memory of the auxiliary components may be non-transitory, allowing retrieval of the data even after the battery has been completely depleted.

Figure 12A:
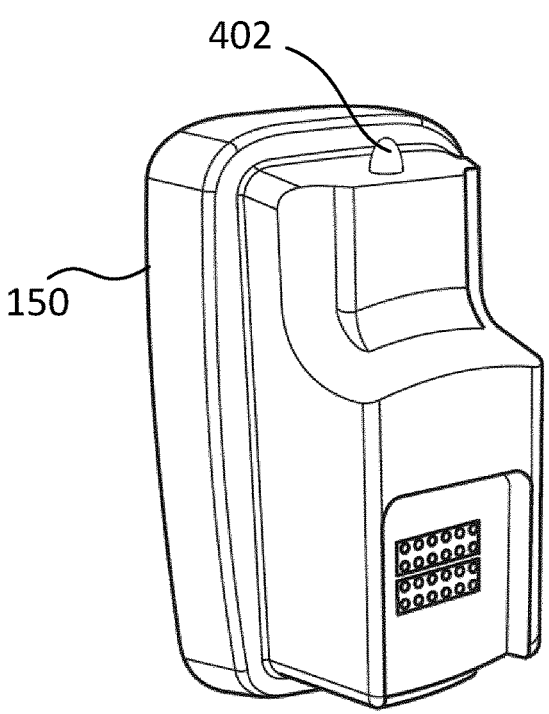
Figure 12B:
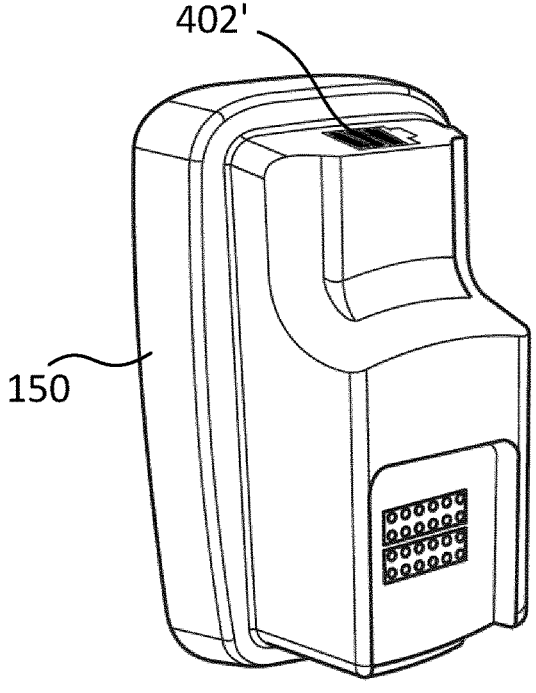

FIGS. 12a and 12b each schematically illustrates an exemplary auxiliary component 150, such as the auxiliary component 150 as described with respect to FIGS. 3a and 3b. The auxiliary component 150, as illustrated, comprises a battery indicator 402, 402'. The battery indicator 402, 402' is indicative of remaining capacity of the battery.

The battery indicator 402, 402' may be an LED or other suitable means for providing an indication of remaining battery capacity. Thereby making the operator aware of when it is necessary to use a different auxiliary component, and consequently when it is needed to transfer the data stored in the auxiliary memory to another auxiliary component, with a more charged battery.

As indicated in FIG. 12a, the battery indicator 402 may comprise an LED, which may indicate the battery capacity by being lit in different colours, e.g. green (indicative of full or near full charge), yellow (medium capacity), red (low capacity). The battery indicator 402 may be flashing, e.g. red, when the battery capacity is below a threshold capacity.

As indicated in FIG. 12b, the battery indicator 402' may comprise a plurality of bars (e.g. five) indicative of capacity of the battery, e.g. fewer bars displayed for less battery capacity. The battery indicator 402' comprising a plurality of bars, may be combined with being lit in different colours, as described above.

The battery indicator 402, 402' may be a button adapted to receive a user input. For example, the user may press the battery indicator 402, 402', and the auxiliary device may be adapted to, in response to receiving the user input on the battery indicator 402, 402' to indicate the present battery capacity. For example, the battery indicator 402 may, in response to receiving the user input, light up the battery indicator 402 in accordance with the current battery capacity. The battery indicator 402' may, in response to receiving the user input on the battery indicator 402, display the plurality of bars in accordance with the current battery capacity. Thus, battery power may be conserved by displaying the indication of battery capacity "on demand" when a user presses the battery indicator 402, 402'. Alternatively or additionally, when the battery capacity is critically low, the battery indicator 402, 402' may indicate battery capacity, e.g. by flashing red, e.g. regardless of receiving or not receiving user input. The battery indicator 402' may be provided using an e-ink display, e.g. such that the battery indicator 402' only uses power when updating the display, e.g. once every day when not being used.

Although the battery indicator 402, 402' is illustrated as being provided on top of the auxiliary device 150, it should be understood that it may be positioned at other convenient positions, depending on the circumstances. For example, the auxiliary component 150 may be a wearable device, such as a wristwatch, wherein the battery indicator may be provided on an outward facing display.

Figure 13:
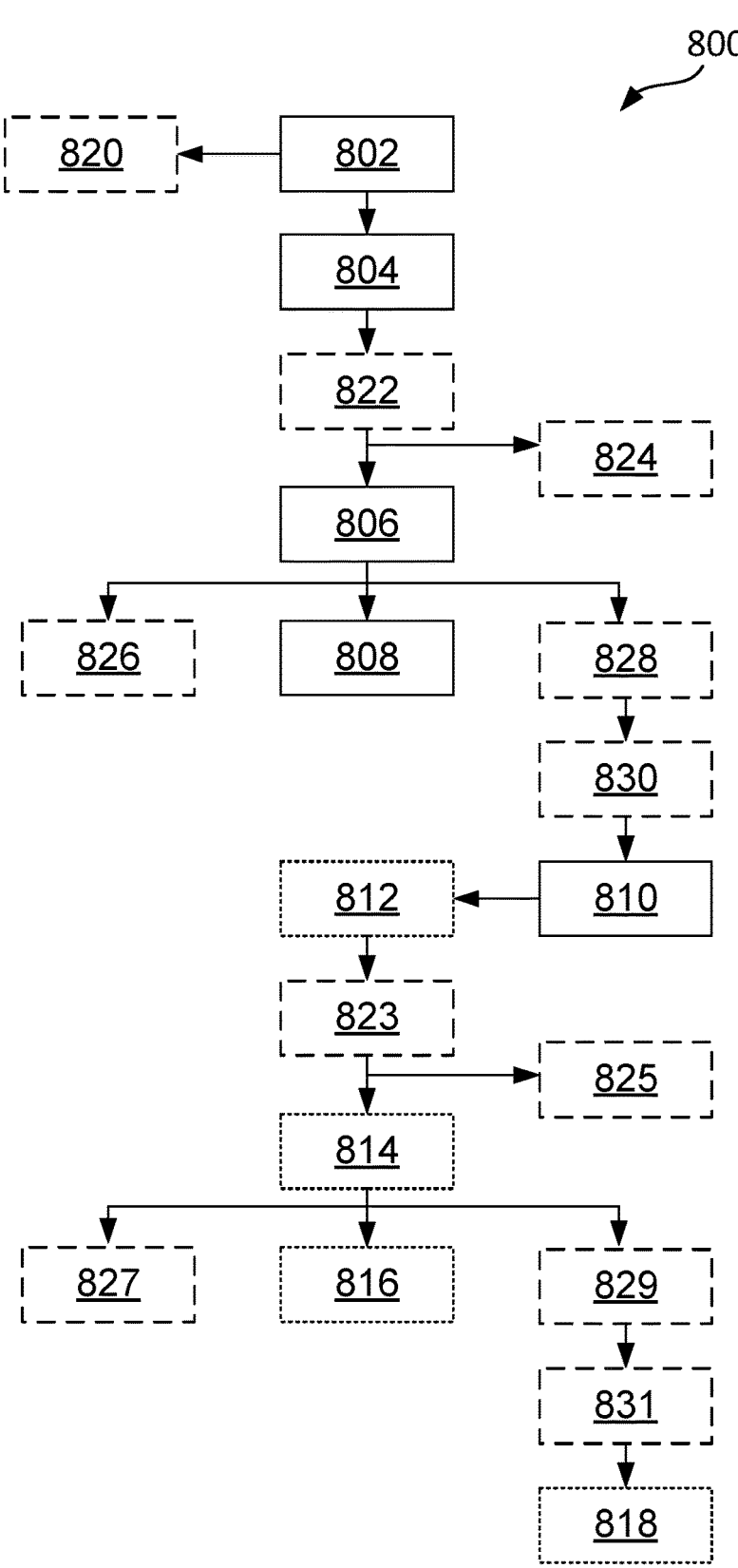
FIG. 13 is a block diagram of an exemplary method for handling auxiliary components.

FIG. 13 is a block diagram of an exemplary method 800 for handling auxiliary components, e.g. including a first auxiliary component 150 and a second auxiliary component 150', as described in relation to the previous figures.

The method 800 comprises receiving 802 a first auxiliary component, e.g. in a first component position of a handling system. The method 800 comprises receiving 804 a second auxiliary component, e.g. in a second component position of a handling system. Receiving 804 the second auxiliary component may be after receiving 802 the first auxiliary component, as illustrated. After receiving 802, 804 the first and second auxiliary component, the method 800 comprises transmitting 806 data, such as initial data, from the auxiliary memory of the second auxiliary component to the auxiliary memory of the first auxiliary component. After transmitting 806 the data from the auxiliary memory of the second auxiliary component to the auxiliary memory of the first auxiliary component, the method 800 comprises providing 810 the first auxiliary component for retrieval, e.g. for the user to retrieve the first auxiliary component, now including a copy of the data previously stored in the auxiliary memory of the second auxiliary component.

After transmitting 806 the data to the auxiliary memory of the first auxiliary component and prior to providing 810 the first auxiliary component for retrieval, the method 800 may comprise validating 828 the data of the auxiliary memory of the first auxiliary component. The method 800 may further comprise, e.g. after validating 828 the data, deleting 830 the data from the auxiliary memory of the second auxiliary component.

The method 800 may comprise receiving 822 a user input at a transmit button, and in response to receiving 822 the user input initiate transmission 806 of the data from the auxiliary memory of the second auxiliary component to the auxiliary memory of the first auxiliary component.

After receiving 802 the first auxiliary component, the method 800 may comprise charging 820 the rechargeable battery of the first auxiliary component.

The method 800 further comprises charging 808 the rechargeable battery of the second auxiliary component. Charging 808 the rechargeable battery of the second auxiliary component may be initiated immediately after receiving 804 the second auxiliary component. Alternatively, as illustrated, charging 808 the rechargeable battery of the second auxiliary component may be performed after transmitting 806 the data.

The method 800 may comprise, e.g. while transmitting 806 the data and/or in response to receiving 822 the user input at the transmit button, storing 824 the data from the auxiliary memory of the second auxiliary component at an external memory.

The method 800 may comprise, e.g. after transmitting 806 the data to the auxiliary memory of the first auxiliary component, disinfecting 826 the second auxiliary component. Although not illustrated, the method 800 may also comprise disinfection of the first auxiliary component, after receipt of the first auxiliary component, e.g. while receiving 804 the second auxiliary component and transmitting 806 the data to the first auxiliary component. In some examples, the first auxiliary component and/or the second auxiliary component may be disinfected before transmitting 806 the data to the first auxiliary component.

The method 800 may further comprise receiving 812 a third auxiliary component, after providing the first auxiliary component for retrieval, and optionally after the first auxiliary component has been retrieved by a user. Hence, the third auxiliary component may be received 812 in the same position as the first auxiliary component was originally received 802. The method 800 may comprise transmitting 814 data from the auxiliary memory of the third auxiliary component to the auxiliary memory of the second auxiliary component. After transmitting 814 the data from the auxiliary memory of the third auxiliary component to the auxiliary memory of the second auxiliary component, the method 800 may comprise providing 818 the second auxiliary component for retrieval.

After transmitting 814 the data to the auxiliary memory of the second auxiliary component and prior to providing 818 the second auxiliary component for retrieval, the method 800 may comprise validating 829 the data of the auxiliary memory of the second auxiliary component. The method 800 may further comprise, e.g. after validating 829 the data, deleting 831 the data from the auxiliary memory of the third auxiliary component.

The method 800 may comprise receiving 823 a user input at a transmit button, e.g. after receiving 812 the third auxiliary component, and in response to receiving 823 the user input initiate transmission 814 of the data from the auxiliary memory of the third auxiliary component to the auxiliary memory of the second auxiliary component.

The method 800 may further comprise charging 816 the rechargeable battery of the third auxiliary component. Charging 816 the rechargeable battery of the third auxiliary component may be initiated immediately after receiving 812 the third auxiliary component. Alternatively, as illustrated, charging 816 the rechargeable battery of the third auxiliary component may be performed after transmitting 814 the data.

The method 800 may comprise, e.g. while transmitting 814 the data and/or in response to receiving 823 the user input at the transmit button, storing 825 the data from the auxiliary memory of the third auxiliary component at the external memory.

The method 800 may comprise, e.g. after transmitting 814 the data to the auxiliary memory of the second auxiliary component, disinfecting 827 the third auxiliary component.

Figure 14:
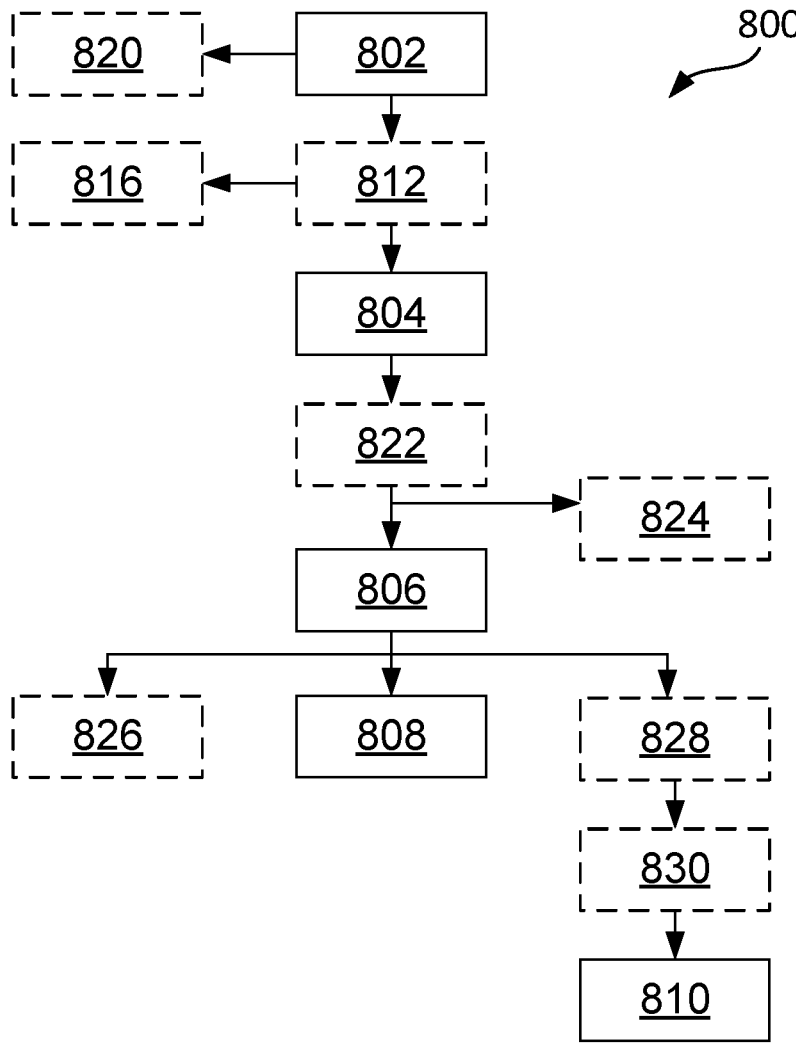
FIG. 14 is a block diagram of an exemplary method for handling auxiliary components.

FIG. 14 is a block diagram of an exemplary method 800' for handling auxiliary components, e.g. including a first auxiliary component 150 and a second auxiliary component 150', as described in relation to the previous figures. The exemplary method 800' comprises similar steps as explained in relation to the exemplary method 800 of FIG. 13, and for simplicity these are not repeated.

However, in the method 800', the third auxiliary component is received 812 after receiving 802 the first auxiliary component but before receiving 804 the second auxiliary component. After receiving 812 the third auxiliary component, the method 800' may comprise charging 816 the rechargeable battery of the third auxiliary component. Thus, the method 800 may receive 812 the third auxiliary component intermediate receipt 802, 804 of the first auxiliary component and the second auxiliary component.

Exemplary embodiments of the present disclosure are set out in the following items:

1. A handling system for handling auxiliary components, including a first auxiliary component and a second auxiliary component, of a medical system, wherein each auxiliary component is adapted to be coupled to a respective main device part, and wherein each auxiliary component comprises a rechargeable battery adapted to power electronic components of the auxiliary component and of the respective main device part, each auxiliary component further comprising an auxiliary memory and an auxiliary communication interface, the handling system comprising a first system communication interface adapted to couple with the auxiliary communication interface of the first auxiliary component and a second system communication interface adapted to couple with the auxiliary communication interface of the second auxiliary component, the handling system being adapted to, via the first system communication interface and/or the second system communication interface, cause transmittal of data from the auxiliary memory of the second auxiliary component to the auxiliary memory of the first auxiliary component, the handling system further comprises a system charging circuit adapted to charge the rechargeable battery of the second auxiliary component.

2. Handling system according to item 1, wherein the handling system comprises a system processing unit, and wherein to transmit the data the system processing unit is adapted to, via the second system communication interface, read or receive the data of the auxiliary memory of the second auxiliary component, and, via the first system communication interface, write or transmit the data from the auxiliary memory of the second auxiliary component to the auxiliary memory of the first auxiliary component.

3. Handling system according to item 1, wherein each of the auxiliary components comprises a short range communication circuit, and wherein the handling system is adapted to, via the first system communication interface and/or the second system communication interface, to cause transmittal of the data from the auxiliary memory of the second auxiliary component to the auxiliary memory of the first auxiliary component by wireless communication between the short range communication circuit of the first auxiliary component and the short range communication circuit of the second auxiliary component.

4. Handling system according to any of the preceding items wherein the system charging circuit includes a first system charging circuit adapted to charge the rechargeable battery of the first auxiliary component and a second system charging circuit adapted to charge the rechargeable battery of the second auxiliary component.

5. Handling system according to any of the preceding items comprising a plurality of component positions including a first component position adapted to receive the first auxiliary component and a second component position adapted to receive the second auxiliary component.

6. Handling system according to any of the preceding items comprising a first transmit button, and wherein the handling system is adapted to cause the transmittal of data from the auxiliary memory of the second auxiliary component to the auxiliary memory of the first auxiliary component, in response to a user pressing the first transmit button.

7. Handling system according to any of the preceding items comprising a second transmit button, and wherein the handling system is adapted to cause transmittal of data from the auxiliary memory of the first auxiliary component to the auxiliary memory of the second auxiliary component, in response to a user pressing the second transmit button.

8. Handling system according to any of the preceding items comprising one or more battery indicators adapted to display a visual indication of estimated battery capacity of the rechargeable battery of the first auxiliary component and/or the second auxiliary component.

9. Handling system according to item 8, wherein the one or more battery indicators includes a first battery indicator adapted to display a visual indication of estimated battery capacity of the rechargeable battery of the first auxiliary component and a second battery indicator adapted to display a visual indication of estimated battery capacity of the rechargeable battery of the second auxiliary component.

10. Handling system according to any of the preceding items, wherein the handling system is connectable to an external memory, and wherein the handling system is adapted to, via the second system communication interface, to read or receive the data from the auxiliary memory of the second auxiliary component and store the data at the external memory.

11. Handling system according to any of the preceding items comprising a disinfection area adapted to disinfect an auxiliary component positioned in the disinfection area, and wherein the handling system is adapted to, after causing transmittal of the data from the auxiliary memory of the second auxiliary component to the auxiliary memory of the first auxiliary component, position the second auxiliary component in the disinfection area.

12. Handling system according to item 11 wherein the disinfection area comprising a chamber wherein an auxiliary component is subjected to ultraviolet radiation, heat, steam, gas and/or a disinfectant.

13. Handling system according to any of the preceding items comprising a conveyor for repositioning the auxiliary components.

14. Handling system according to any of the preceding items adapted to validate the data of the auxiliary memory of the first auxiliary component after transmittal of the data to the auxiliary memory of the first auxiliary component.

15. Handling system according to any of the preceding items adapted to delete the data from the auxiliary memory of the second auxiliary component after transmittal of the data to the auxiliary memory of the first auxiliary component.

16. A method for handling auxiliary components, including a first auxiliary component and a second auxiliary component, of a medical system, wherein each auxiliary component is adapted to be coupled to a respective main device part, and wherein each auxiliary component comprises a rechargeable battery adapted to power electronic components of the auxiliary component and of the respective main device part, each auxiliary component further comprising an auxiliary memory and an auxiliary communication interface, the method comprises receiving a first auxiliary component, receiving a second auxiliary component, transmitting data from the auxiliary memory of the second auxiliary component to the auxiliary memory of the first auxiliary component, charging the rechargeable battery of the second auxiliary component, and providing the first auxiliary component for retrieval after transmitting the data from the auxiliary memory of the second auxiliary component to the auxiliary memory of the first auxiliary component.

17. Method according to item 16, wherein the second auxiliary component is received after receiving the first auxiliary component.

18. Method according to any of items 16-17 further comprising:

receiving a third auxiliary component after providing the first auxiliary component for retrieval, transmitting the data from the auxiliary memory of the third auxiliary component to the auxiliary memory of the second auxiliary component, charging the rechargeable battery of the third auxiliary component, and providing the second auxiliary component for retrieval after transmitting the data from the auxiliary memory of the third auxiliary component to the auxiliary memory of the second auxiliary component.

19. Method according to any of items 16-17 further comprising:

receiving a third auxiliary component after receiving the first auxiliary component and before receiving the second auxiliary component, charging the rechargeable battery of the third auxiliary component.

20. Method according to any of items 16-19 comprising, after receiving the first auxiliary component, charging the rechargeable battery of the first auxiliary component.

21. Method according to any of items 16-20 comprising receiving a user input at a transmit button, and in response to receiving the user input transmitting the data from the auxiliary memory of the second auxiliary component to the auxiliary memory of the first auxiliary component.

22. Method according to any of items 16-21 comprising storing the data from the auxiliary memory of the second auxiliary component at an external memory.

23. Method according to any of items 16-22 comprising, after transmitting the data to the auxiliary memory of the first auxiliary component, disinfecting the second auxiliary component.

24. Method according to any of items 16-23 comprising, after transmitting the data to the auxiliary memory of the first auxiliary component, validating the data of the auxiliary memory of the first auxiliary component.

25. Method according to any of items 16-24 comprising, after transmitting the data to the auxiliary memory of the first auxiliary component, deleting the data from the auxiliary memory of the second auxiliary component.

26. Medical system comprising auxiliary components, including a first auxiliary component and a second auxiliary component, wherein each auxiliary component is adapted to be coupled to a respective main device part, and wherein each auxiliary component comprises an auxiliary memory and a short range communication circuit and an auxiliary user interface, and wherein the first auxiliary component and second auxiliary component are adapted to transmit, via the short range communication circuits, data from the auxiliary memory of the second auxiliary component to the auxiliary memory of the first auxiliary component, in response to receiving, at the auxiliary user interface (s) of the first auxiliary component and/or second auxiliary component, one or more user inputs indicative of a request to transmit the data from the auxiliary memory of the second auxiliary component to the auxiliary memory of the first auxiliary component.

27. Medical system according to item 26, wherein the one or more user inputs indicative of a request to transmit the data from the auxiliary memory of the second auxiliary component to the auxiliary memory of the first auxiliary component comprises receiving a first user input at the auxiliary user interface of the first auxiliary component and while or after receiving the first user input at the auxiliary user interface of the first auxiliary component receiving a second user input at the auxiliary user interface of the second auxiliary component.

28. Medical system comprising the handling system according to any of items 1-15 and the first auxiliary component and the second auxiliary component.

The disclosure has been described with reference to a preferred embodiment. However, the scope of the invention is not limited to the illustrated embodiment, and alterations and modifications can be carried out without deviating from the scope of the invention.

Throughout the description, the use of the terms "first", "second", "third", "fourth", "primary", "secondary", "tertiary" etc. does not imply any particular order or importance but are included to identify individual elements. Furthermore, the labelling of a first element does not imply the presence of a second element and vice versa.

LIST OF REFERENCES 2 medical visualisation system
4 downstream data channel
6 upstream data channel
8 operator
10 patient
100, 100' medical visualisation device
110 main device part
112 image sensor
114 view
116 light emitter
118 handle
119 device button, e.g. image capture button
120 insertion tube
122 distal tube portion
124 control button
125A first input direction
125B second input direction
126 bendable section
128A first bending direction
128B second bending direction
130 main coupling part
132 main terminal
134 safety circuit
136 device identifier
140 main surface
142 main primary engagement member
146 primary surface
150 auxiliary component
152 auxiliary housing
154 device processing unit
155 auxiliary memory
156 device wireless communication module
158 device antenna
160 battery
170 auxiliary coupling part
172 auxiliary terminal
182 auxiliary primary engagement member 200 monitor device
202 first housing
204 display
206 monitor wireless communication module
207 monitor antenna
208 monitor processing unit
210 monitor memory
212 monitor button, e.g. image capture button
300 operating room
302 operating setting
304 ceiling
402, 402' battery indicator
500 auxiliary communication interface
502 short range communication circuit
510 initial data
512 patient data
514 operator data
516 operator setup data
516A parameters
516B button setting
516C voice control data
700 handling system
702A, 702B system communication interface
704A, 704B system charging circuit
706 system processing unit
710A, 710B component position
712A, 712B transmit button
714A, 714B battery indicator
716 external memory
718 disinfection area
720 conveyor belt
730, 730' auxiliary user interface
800, 800' method
802 receiving first auxiliary component
804 receiving second auxiliary component
806 transmitting data
808 charging rechargeable battery
810 providing first auxiliary component
812 receiving third auxiliary component
814 transmitting data
816 charging rechargeable battery
818 providing second auxiliary component
820 charging rechargeable battery
822, 823 receiving user input
824, 825 storing data on external memory
826, 827 disinfecting
828, 829 validating data
830, 831 deleting data

The invention claimed is:

1. A handling system for handling auxiliary components, including a first auxiliary component and a second auxiliary component, of a medical system, each of the auxiliary components including an auxiliary memory, an auxiliary communication interface, and a rechargeable battery configured to power electronic components of the auxiliary component and of a main device component when coupled to the auxiliary component, the handling system comprising:

a first system communication interface configured to couple with the auxiliary communication interface of the first auxiliary component;

a second system communication interface configured to couple with the auxiliary communication interface of the second auxiliary component; and a system charging circuit configured to charge the rechargeable battery of the second auxiliary component, wherein the handling system is configured to, via the first system communication interface and the second system communication interface, cause transmittal of data from the auxiliary memory of the second auxiliary component to the auxiliary memory of the first auxiliary component.

2. The handling system of claim 1, wherein the handling system comprises a system processor configured to, via the second system communication interface, read or receive the data of the auxiliary memory of the second auxiliary component, and, via the first system communication interface, write or transmit the data to the auxiliary memory of the first auxiliary component.

3. The handling system of claim 1, wherein each of the auxiliary components comprises a short range communication circuit, and wherein the handling system is configured, via the first system communication interface and the second system communication interface, to cause transmittal of the data from the auxiliary memory of the second auxiliary component to the auxiliary memory of the first auxiliary component by wireless communication between the short range communication circuit of the first auxiliary component and the short range communication circuit of the second auxiliary component.

4. The handling system of claim 1, wherein the system charging circuit includes a first system charging circuit configured to charge the rechargeable battery of the first auxiliary component and a second system charging circuit configured to charge the rechargeable battery of the second auxiliary component.

5. The handling system of claim 1, the handling system further comprising a plurality of component positions including a first component position configured to receive the first auxiliary component and a second component position configured to, concurrently, receive the second auxiliary component.

6. The handling system of claim 1, the handling system further comprising a first transmit button, wherein the handling system is configured to cause the transmittal of the data from the auxiliary memory of the second auxiliary component to the auxiliary memory of the first auxiliary component, in response to a user pressing the first transmit button.

7. The handling system of claim 6, the handling system further comprising a first transmit button and a second transmit button, wherein the handling system is configured to cause transmittal of data from the auxiliary memory of the first auxiliary component to the auxiliary memory of the second auxiliary component, in response to a user pressing the second transmit button.

8. The handling system of claim 1, the handling system further comprising one or more battery indicators configured to display a visual indication of an estimated battery capacity of the rechargeable battery of the first auxiliary component and/or the second auxiliary component.

9. The handling system of claim 1, wherein the handling system is connectable to an external memory, and wherein the handling system is configured to, via the second system communication interface, read or receive the data from the auxiliary memory of the second auxiliary component and store the data at the external memory.

10. The handling system of claim 1, wherein the handling system further comprises a disinfection area including a chamber configured to subject the second auxiliary component to ultraviolet radiation, heat, steam, gas and/or a disinfectant, and wherein the handling system is configured to, after causing transmittal of the data, position the second auxiliary component in the chamber and disinfect the second auxiliary component.

11. The handling system of claim 1, wherein the handling system is further configured to validate the data transferred to the auxiliary memory of the first auxiliary component.

12. The handling system of claim 1, wherein the handling system is further configured to delete the data from the auxiliary memory of the second auxiliary component after transmittal of the data to the auxiliary memory of the first auxiliary component.

13. The handling system of claim 12, wherein the handling system is further configured to validate the data transferred to the auxiliary memory of the first auxiliary component before deleting the data from the auxiliary memory of the second auxiliary component.

14. A method for handling auxiliary components, including a first auxiliary component and a second auxiliary component, of a medical system, each of the auxiliary components comprising an auxiliary memory, an auxiliary communication interface, and a rechargeable battery configured to power the auxiliary component and a main device component coupled to the auxiliary component, the method comprising:
    coupling the first auxiliary component to the first system communication interface of the handling system of claim 1,
    coupling the second auxiliary component to the second system communication interface of the handling system of claim 1,
    transmitting the data from the auxiliary memory of the second auxiliary component to the auxiliary memory of the first auxiliary component, and
    charging the rechargeable battery of the second auxiliary component.

15. The method of claim 14, wherein coupling the second auxiliary component is performed after coupling the first auxiliary component.

16. The method of claim 14, further comprising, after coupling the first auxiliary component, charging the rechargeable battery of the first auxiliary component and providing the first auxiliary component for retrieval after transmitting the data from the auxiliary memory of the second auxiliary component to the auxiliary memory of the first auxiliary component.

17. The method of claim 14, further comprising storing the data from the auxiliary memory of the second auxiliary component at an external memory.

18. The method of claim 14, further comprising, after transmitting the data to the auxiliary memory of the first auxiliary component, validating the data of the auxiliary memory of the first auxiliary component and deleting the data from the auxiliary memory of the second auxiliary component.

19. A medical system comprising:
    the handling system of claim 1;
    the main component; and
    the auxiliary components,
    wherein the auxiliary components comprise the first auxiliary component and the second auxiliary component.

20. The medical system of claim 19, wherein the handling system is further configured to validate the data transferred to the auxiliary memory of the first auxiliary component and, after said validating, to delete the data from the auxiliary memory of the second auxiliary component.

21. A medical system comprising:
    a main device component;

auxiliary components configured to be coupled to the main device component, including a first auxiliary component and a second auxiliary component, each of the auxiliary components comprising an auxiliary memory, a short range communication circuit and an auxiliary user interface, wherein the second auxiliary component is configured to transmit, via the short range communication circuit of the second auxiliary component to the short range communication circuit of the first auxiliary component, data from the auxiliary memory of the second auxiliary component to the auxiliary memory of the first auxiliary component, in response to receiving, at the auxiliary user interface(s) of the first auxiliary component and/or the second auxiliary component, one or more user inputs indicative of a request to transmit the data from the auxiliary memory of the second auxiliary component to the auxiliary memory of the first auxiliary component.

22. The medical system of claim 21, wherein the one or more user inputs indicative of a request to transmit the data comprises receiving a first user input at the auxiliary user interface of the first auxiliary component and while or after receiving the first user input at the auxiliary user interface of the first auxiliary component receiving a second user input at the auxiliary user interface of the second auxiliary component.

23. A medical system comprising:

a medical device comprising a main device component and a first auxiliary component physically and removably attachable to the main device component, the main device component further comprising a camera at a distal end thereof, and the first auxiliary component comprising a first memory, a first short range communication circuit, a first user interface, and a first rechargeable battery configured to power the first auxiliary component and the main device component; and a second auxiliary component physically and removably attachable to the main device component, the second auxiliary component comprising a second memory, a second short range communication circuit, a second user interface, and a second rechargeable battery configured to power the second auxiliary component and the main device component, the second memory comprising initial data consisting of patient data and/or operator data and/or operator setup data, wherein the second auxiliary component is configured to transmit the initial data, via the second short range communication circuit to the first short range communication circuit of the first auxiliary component in response to receiving one or more user inputs indicative of a request to transmit the initial data, at the first auxiliary user interface or the second auxiliary user interface.

24. The medical system of claim 23, wherein the one or more user inputs comprise a first user input received at the first user interface while or after receiving a second user input at the second user interface.

* * * * *